United States Patent
Gross et al.

(10) Patent No.: US 9,790,259 B2
(45) Date of Patent: *Oct. 17, 2017

(54) BIS-MET HISTONES

(71) Applicant: Symbiotec Genellschaft zur Erforschung auf dem Geibeit der Biotechnologie, MBH, Saarbrucken (DE)

(72) Inventors: Peter Gross, Bexbach (DE); Hans Jornvall, Stockholm (SE); Grazyna Formicka-Zeppezauer, Saarbrucken (DE); Michael Zeppezauer, Saarbrucken (DE); Michel Thiry, Trooz (BE)

(73) Assignee: Symbiotec Genellschaft zur Erforschung auf dem Geibeit der Biotechnologie, MBH, Saarbrucken (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/001,214

(22) Filed: Jan. 19, 2016

(65) Prior Publication Data

US 2016/0130313 A1     May 12, 2016

Related U.S. Application Data

(63) Continuation of application No. 12/594,664, filed as application No. PCT/EP2008/002746 on Apr. 7, 2008, now Pat. No. 9,409,960.

(30) Foreign Application Priority Data

Apr. 5, 2007 (EP) .................................... 07007200
Sep. 26, 2007 (EP) .................................... 7018956

(51) Int. Cl.
  *A61K 38/00*     (2006.01)
  *C07K 14/47*     (2006.01)

(52) U.S. Cl.
  CPC .............. *C07K 14/47* (2013.01); *A61K 38/00* (2013.01); *Y10T 436/143333* (2015.01)

(58) Field of Classification Search
  None
  See application file for complete search history.

(56) References Cited

U.S. PATENT DOCUMENTS 5,637,465 A    6/1997  Trauth
9,409,960 B2 * 8/2016  Gross ..................... C07K 14/47

FOREIGN PATENT DOCUMENTS

EP      1114865 B1      7/2001
WO      20010051511 A1  7/2001

OTHER PUBLICATIONS

Hirel, P-H, et al., "Extent of N-terminal methionine excision from *Escherichia coli* proteins is governed by the side-cain length of the penultimate amino acid," Proc. Natl. Acad. Sci., of USA, Natl. Acad. Sci. of Washingtin DC, US, Nov. 1989, pp. 8247-8251, vol. 86, No. 21.
International Search Report, PCT/EP08/02746, mailed Aug. 19, 2008.
Jerala R., et al., "Cloning a Synthetic Gene for Human Stefin B and its Expression in *E. Coli*," Febs Letters, Elsevier, Amsterdam, NL, Oct. 24, 1988, pp. 41-44, vol. 239, No. 1.

* cited by examiner

*Primary Examiner* — Jim Ketter
(74) *Attorney, Agent, or Firm* — Entralta P.C.; Annette S. Parent; Peter D. Weinstein

(57) ABSTRACT

The present invention provides a nucleic acid molecule which encodes a polypeptide consisting of two methionine residues as the first and second N-terminal amino acid residues linked via a peptide bond to a mature eukaryotic histone. The present invention furthermore relates to a vector containing said nucleic acid molecule, a host transformed with said vector, polypeptides encoded by the nucleic acid molecule and pharmaceutical and diagnostic compositions. The present invention also relates to the use of the nucleic acid molecule, vectors, hosts and the polypeptide of the invention for the preparation of a composition for the treatment of diseases. Furthermore, the present invention relates to a method of testing for the presence of the nucleic acid molecule or the polypeptide in a sample and to a kit.

21 Claims, 3 Drawing Sheets

BIS-MET HISTONES

Figure 1:
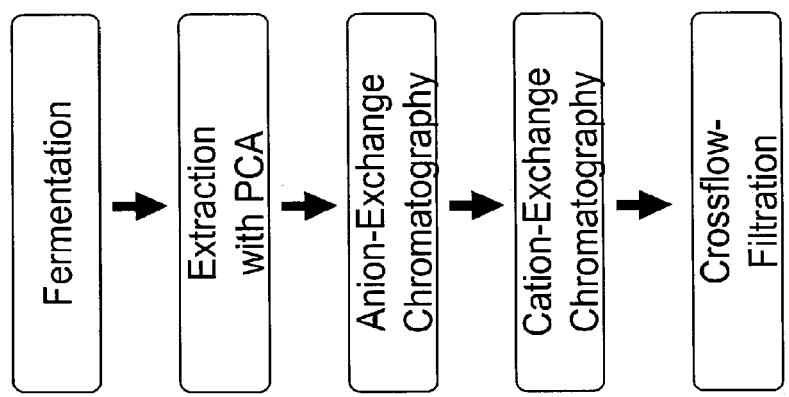

This application is a continuation that claims the benefit of priority pursuant to 35 U.S.C. §120 to U.S. patent application Ser. No. 12/594,664, filed on Oct. 19, 2010, which is a 35 U.S.C. §371 national stage filing of PCT/EP2008/002746, filed on Apr. 7, 2008, which claims priority to European Patent Application EP 7018956.8, filed on Sep. 26, 2007 and European Patent Application EP 07007200.4, filed on Apr. 5, 2007, each of which is hereby incorporated by reference in its entirety.

The present invention provides a nucleic acid molecule which encodes a polypeptide consisting of two methionine residues as the first and second N-terminal amino acid residues linked via a peptide bond to a mature eukaryotic histone. The present invention furthermore relates to a vector containing said nucleic acid molecule, a host transformed with said vector, polypeptides encoded by the nucleic acid molecule and pharmaceutical and diagnostic compositions. The present invention also relates to the use of the nucleic acid molecule, vectors, hosts and the polypeptide of the invention for the preparation of a composition for the treatment of diseases. Furthermore, the present invention relates to a method of testing for the presence of the nucleic acid molecule or the polypeptide in a sample and to a kit.

A variety of documents is cited throughout this specification. The disclosure content of said documents including manufacturer's manuals is herewith incorporated by reference in its entirety.

Currently, there is an enormous economic interest in high level production of recombinant proteins, such as histones. Production of large quantities of recombinant proteins is not only of interest for the purpose of providing a sufficient amount of protein for studies into their properties and functions, but also for the provision of large amounts of protein for therapeutic use.

An extensive amount of parameters has to be taken into consideration for the successful high level production and purification of recombinant proteins. Important parameters include expression conditions, translational regulation and mRNA stability, protein targeting and degradation (Makrides, S., Microbiological Reviews, 1996: 512).

One approach in order to improve the production, detection and purification of recombinant proteins is the use of a wide variety of fusion partners (Makrides, S., Microbiological Reviews, 1996: 512). Elaborate techniques have been developed to include affinity-tags for the purification and detection of recombinant proteins. Such affinity tags combine the advantageous properties of allowing for a more efficient purification while also allowing for an easy detection of the recombinant protein based on the tag. However, in many instances the addition of a rather large affinity tag may be disadvantageous due to unwanted effects on protein translation, folding and activity. Especially for the use in therapeutic applications subsequent removal of the affinity tag is often necessary, thus alleviating some of the positive effects (e.g. easy detection) the affinity tag confers onto the protein (Gellissen, G. "Production of Recombinant Proteins", 2005, WILEY-VCH Verlag GmbH&Co., KgaA, Weinheim).

Incorporation of a methionine residue at the N terminus of each nascent polypeptide constitutes part of the universal translation initiation signal, used by prokaryotes as well as eukaryotes. In *E. coli*, removal of this N-terminal methionine residues is achieved by the cytoplasmic enzyme methionine aminopeptidase (map) (Hirel et al., Biochemistry, 1989, 86:8247).

Efficient processing of the N-terminal methionine residue of recombinant eukaryotic proteins produced in prokaryotes, e.g. in *E. coli*, has been shown to depend on the amino acid adjacent to the methionine. Although there are conflicting data for some of the amino acids there seems to be agreement that cleavage probability is highest for the small and uncharged amino acid residues Ala, Gly, Pro, Ser, Val, Cys and Thr. Larger side chains seem to be disadvantageous for methionine processing (Hirel et al., Biochemistry, 1989, 86:8247; Frottin et al., Mol. & Cell. Proteomics, 2006, 12:2336; Gellissen, G. "Production of Recombinant Proteins", 2005, WILEY-VCH Verlag GmbH&Co., KgaA, Weinheim).

Processing of N-terminal methionine is thought to play important roles for protein stability (Giglione et al., EMBO J., 2003, 1:13) but also for the correct function of the protein, as shown for example for MEF-2C, human hemoglobin, interleukin-2, RNase A homologues or frog ribonuclease (Meierhans and Allemann, J. Biol. Chem., 1998, 273:26052; Adachi, K. et al., Protein Expr. Purif., 2000, 20:37; Endo, S. et al., Biochemistry, 2001, 40:914; Boix, E. et al., J. Mol. Biol., 1996, 257:992; Liao, Y. D. et al., Nucleic Acids Res., 2003, 31:5247; Varshaysky, A., Proc., Natl. Acad. Sci., 1996, 93:12142). An additional theory as to why nature has retained such a specialized enzymatic system to remove the methionine residue is for recycling of the cellular methionine pool to economize this essential amino acid (Hirel et al., Biochemistry, 1989, 86:8247).

EP1254166 describes the recombinant production of histone proteins in *E. coli*. Such recombinant production of human proteins is considered advantageous for therapeutic applications as well as more efficient and cost effective as compared to human or calf thymus preparations. Furthermore, the recombinant production of proteins allows better quality control during the production process.

Pyo et al. (Pyo, S. H. et al., Protein Expr. Purif., 2001, 1:38) describes the production of recombinant histone H1.5 in *E. coli* using the strongly basic properties of the histone to develop an efficient method for large-scale purification of recombinant protein.

Although high level production of recombinant proteins has been shown in the prior art there is nonetheless a substantial need to find suitable methods of detecting the resulting recombinant protein. As discussed above, the use of affinity tags, such as his-tags, is widely used in the art but can be problematic for the production of proteins for therapeutic use.

Thus, the technical problem underlying the present invention was to provide improved recombinant eukaryotic polypeptides that, for example, allow a simplification of production and detection.

The solution to this technical problem is achieved by the embodiments characterized in the claims.

Accordingly, the present invention relates in a first embodiment to a nucleic acid molecule which (a) encodes a polypeptide consisting of (aa) two methionine residues as the first and second N-terminal amino acid residues linked via a peptide bond to (ab) a mature eukaryotic histone; (b) encodes a polypeptide consisting of (ba) two methionine residues as the first and second N-terminal amino acid residues linked via a peptide bond to (bb) a mature eukaryotic polypeptide having at least 80% sequence identity to the mature eukaryotic histone of (a) and essentially retaining its biological activity; or (c) hybridizes under stringent conditions to the complementary strand of a nucleic acid molecule encoding the polypeptide of (a) or (b), wherein said nucleic acid molecule encodes a polypeptide having at least the two N-terminal methionine residues and essentially retains the biological activity of the polypeptide of (a) or (b).

Nucleic acid molecules, in accordance with the present invention, include DNA, such as cDNA or genomic DNA, RNA (e.g. mRNA), also in synthetic or semisynthetic form, further synthetic or semisynthetic derivatives of DNA or RNA (e.g. PNA or phosphorothioates) and mixed polymers, both sense and antisense strands. They may contain additional non-natural or derivatized nucleotide bases, as will be readily appreciated by those skilled in the art. In a preferred embodiment nucleic acid molecule is DNA, including genomic DNA.

For the purposes of the present invention, a peptide nucleic acid (PNA) is a polyamide type of DNA analog and the monomeric units for the derivatives of adenine, guanine, thymine and cytosine are available commercially (Perceptive Biosystems). Certain components of DNA, such as phosphorus, phosphorus oxides, or deoxyribose derivatives, are not present in PNAs. As disclosed by Nielsen et al., Science 254:1497 (1991); and Egholm et al., Nature 365:666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point ($T_m$) by 8°-20° C., vs. 4°-16° C. for the DNA/DNA 15-mer duplex. Also, the absence of charge groups in PNA means that hybridization can be done at low ionic strengths and reduce possible interference by salt during the analysis.

The term "polypeptide" as used herein describes a group of molecules which consist of more than 30 amino acids. In accordance with the invention, the group of polypeptides comprises "proteins". Polypeptides may further form dimers, trimers and higher oligomers, i.e. consisting of more than one polypeptide molecule. Polypeptide molecules forming such dimers, trimers etc. may be identical or non-identical. The corresponding higher order structures are, consequently, termed homo- or heterodimers, homo- or heterotrimers etc. Homo- or heterodimers etc. also fall under the definition of the term "protein". Polypeptides may further be fusion proteins, wherein the fusion partner is attached C-terminally to the polypeptide of the invention. Those components of said fusion proteins, which are not histone sequences or fragments or variants thereof as defined herein above, include amino acid sequence which confer desired properties such as modified/enhanced stability, modified/enhanced solubility and/or the ability of targeting one or more specific cell types or could confer a different biological activity. For example, fusion proteins with antibodies specific for cell surface markers or with antigen-recognizing fragments of said antibodies are envisaged. Furthermore, peptidomimetics of such polypeptides wherein amino acid(s) and/or peptide bond(s) have been replaced by functional analogs are also encompassed by the invention. Such functional analogues include all known amino acids other than the 20 gene-encoded amino acids, such as selenocysteine. The terms "polypeptide" and "protein" also refer to naturally modified polypeptides/proteins wherein the modification is effected e.g. by glycosylation, acetylation, phosphorylation and the like. Such modifications are well known in the art.

The term "methionine", in accordance with the present invention, is well known to the person skilled in the art. Methionine is an essential amino acid encoded by the codon AUG in the standard genetic code. Said methionine, as it is found in eukaryotes, is contributing to a preferred embodiment of the invention. Also encompassed within the meaning of the term methionine, and contributing to an alternative embodiment of the invention, is the N-formylmethionine of prokaryotes.

The term "first and second N-terminal amino acid residue" as used herein refers to the amino acid residues found in positions 1 and 2 of the polypeptide of the invention. These residues are also referred to in the art as the ultimate and penultimate residue at the N terminus. In other terms, the first methionine residue is positioned N-terminally of the initial translation product of the polypeptide which itself contains a methionine at its N-terminus.

The term "peptide bond" as used herein is well known to the person skilled in the art and refers to the chemical bond formed between two amino acid molecules wherein the carboxyl group of one amino acid reacts with the amino group of the other amino acid.

The term "mature eukaryotic histone", in accordance with the present invention, refers to a histone devoid of its initial N-terminal methionine. As is well known to the person skilled in the art, polypeptides are translated using a universal translation initiation signal which leads to the incorporation of methionine as the initial amino acid residue of the N terminus of the translated polypeptide. In eukaryotes, and partially also in prokaryotes, this N-terminal methionine is cleaved off resulting in the "maturation" of the polypeptide.

In accordance with the present invention, the term "histone" refers to a group of proteins including the core histones H2A (the Swiss-Prot Number for human H2A is P02261), H2B (the Swiss-Prot Number for human H2B is P02278), H3 (the Swiss-Prot Number for human H3.1 is P16106) and H4 (the Swiss-Prot Number for human H4 is P02304) and the H1 linker histone family (see below for Swiss-Prot numbers). Histones are classically known as structural components of the cell nucleus where they act as "spools" around which DNA is wound and play a key role in gene regulation. However, histones demonstrate a broad multi functionality (Reichhart, R. et al., Proc. Natl. Acad. Sci. 1985, 82:4871; Reichhart, R. et al., FEBS 1985, 188: 63). For example, histones have been found to act systemically as hormones and regulatory factors, and are also carriers of important protective functions.

Due to their broad multi-functionality histones have become important in a number of therapeutic approaches. For example, histones H1, H2A and H2B have been found to stimulate peripheral healthy lymphocytes (Cebecauer, L. et al. Rheumatologia 1991, 5:107). Histone H1 has been found to improve muscle regeneration by stimulating proliferation of myoblasts (Henriquez, J. P. et al., J. Cell Sci. 2002, 115:2041), to modulate the state of diseases with amyloid-like fibrils (Duce, J. A. et al. J. Mol. Biol. 2006, 361:493) and to stimulate stem cells (Semina et al. Radiation Biology and Oncology, 1994, 34:544). Histone H1 can also be used to diagnose, prevent and treat ulcerative colitis and clinical subtypes thereof (Braun, J. et al., U.S. Pat. No. 6,074,835). Histone H1 as well as cores histones have furthermore be found to be able to transport biologically active substances through the blood-brain barrier (Pardridge, W. M. et al., J. Pharmacol. Exp. Ther. 1989, 251:821). Furthermore, European patent 0392315 shows a hormone or hormone like activity of histone H1 and its subtypes. A role of histone in autoimmune diseases including, for example, systemic lupus (SLE) has been shown, e.g. in European patent 0532979 or the patent application WO 03/044054. Further functions of histones have been shown to include antibiotic functions (U.S. Pat. Nos. 6,565,854 and 6,884, 423) and antiviral functions (WO 2005/112975). In addition, use of histones in preventing platelet aggregation (WO02/ 067907) or for the treatment of thrombocytopenia (WO/ 2006/119912) has been shown.

Histones have also been found to play a pivotal role in the treatment of cancer. Vani et al. (Vani, G. et al., Chemotherapy 2003, 49:252) show for example, that histone H1 improves the immune status and immune response in animals bearing experimental breast carcinoma. Also the antioxidant status in individuals suffering from cancer has been shown to be enhanced by histone H1 (Vani, G. et al., Chemotherapy 2005, 51: 57). Treatment of human estrogen sensitive breast cancer cells with histone H1 has also been shown to reduce the number of estrogen receptors (Vani, G. and Devi, C. S., Mol. Cell Biochem. 2005, 272:151). The treatment of radiation-induced leukemia or carcinoma with histones H1 or H2A:H2B is shown in U.S. Pat. No. 5,812, 257. Histones may also potentially be useful in the treatment of cancer by scavenging pathogenic extracellular DNA and systemic circulating pathogenic nucleosomes (Le Lann-Terrisse et al. (1997) Cancer Immunol Immunother, 43:337).

In accordance with the present invention the nucleic acid molecule can also encode a polypeptide consisting of two methionine residues as the first and second N-terminal amino acid residues linked via a peptide bond to a mature eukaryotic polypeptide having at least 80% sequence identity, more preferably 85%, more preferably 90% sequence identity to the mature eukaryotic histone of (a) and essentially retaining its biological activity. Even more preferably the nucleic acid molecule can encode a polypeptide consisting of two methionine residues as the first and second N-terminal amino acid residues linked via a peptide bond to a mature eukaryotic polypeptide having at least 95% sequence identity and most preferably 98% sequence identity to the mature eukaryotic histone of (a) and retaining its biological function.

In accordance with the present invention, the term "percent sequence identity" describes the number of matches ("hits") of identical nucleotides/amino acids of two or more aligned nucleic acid or amino acid sequences as compared to the number of nucleotides or amino acid residues making up the overall length of the nucleic acid or amino acid sequences (or the overall compared, part thereof). In other terms, using an alignment, for two or more sequences or subsequences the percentage of amino acid residues or nucleotides that are the same (e.g., 80% or 85% identity) may be determined, when the (sub)sequences are compared and aligned for maximum correspondence over a window of comparison, or over a designated region as measured using a sequence comparison algorithm as known in the art, or when manually aligned and visually inspected. This definition also applies to the complement of a test sequence. Preferred nucleic acid molecules/polypeptides in accordance with the invention are those where the described identity exists over a region that is at least about 15 to 25 amino acids or nucleotides in length, more preferably, over a region that is about 50 to 100 amino acids or nucleotides in length. Those having skill in the art will know how to determine percent sequence identity between/among sequences using, for example, algorithms such as those based on CLUSTALW computer program (Thompson Nucl. Acids Res. 2 (1994), 4673-4680) or FASTA (Pearson and Lipman, Proc. Natl. Acad. Sci., 1988, 85; 2444), as known in the art.

Although the FASTDB algorithm typically does not consider internal non-matching deletions or additions in sequences, i.e., gaps, in its calculation, this can be corrected manually to avoid an overestimation of the % sequence identity. CLUSTALW, however, does take sequence gaps into account in its identity calculations. Also available to those having skill in this art are the BLAST and BLAST 2.0 algorithms (Altschul, Nucl. Acids Res., 1977, 25:3389). The BLASTN program for nucleic acid sequences uses as default a word length (W) of 11, an expectation (E) of 10, M=5, N=4, and a comparison of both strands. For amino acid sequences, the BLASTP program uses as default a word length (VW) of 3, and an expectation (E) of 10. The BLOSUM62 scoring matrix (Henikoff, Proc. Natl. Acad. Sci., 1989, 89:10915) uses alignments (B) of 50, expectation (E) of 10, M=5, N=4, and a comparison of both strands. All those programs may be used for the purposes of the present invention. All of the above programs can be used in accordance with the invention.

In accordance with the present invention, activity is essentially retained, if at least 20% of the biological activity of the corresponding mature eukaryotic histone recited in item (a), supra, is obtained. Preferably, at least 50%, such as at least 60%, at least 75% or at least 80% of the activity are retained. More preferred is that at least 90% such as at least 95%, even more preferred at least 98% such as at least 99% of the biological activity are retained. Most preferred is that the biological activity is fully, i.e. to 100%, retained. Also in accordance with the invention are polypeptides having increased biological activity compared to the corresponding mature eukaryotic histone recited in (a), i.e. more than 100% enzyme activity of the reference histone. Methods of assessing biological activity of a (poly)peptide are well known to the person skilled in the art and include without being limiting measuring enzymatic activity, cytotoxicity, cytokine release, hemolysis or the expression of biomarkers. In particular, cytotoxicity tests are tests with in vitro or in vivo cell cultures, which are treated e.g. by (poly)peptide, for example histones, and wherein the gradient of mortality of the cells is determined with cell detection methods after the treatment. Biological activity can also be determined with ELISA tests, especially in the case of antibodies.

The term "hybridizes/hybridizing" as used herein refers to a pairing of a nucleic acid molecule to a (partially) complementary strand of this nucleic acid molecule which thereby form a hybrid.

It is well known in the art how to perform hybridization experiments with nucleic acid molecules. Correspondingly, the person skilled in the art knows what hybridization conditions they have to use to allow for a successful hybridization. The establishment of suitable hybridization conditions is referred to in standard text books such as Sambrook and Russell "Molecular Cloning, A Laboratory Manual", Cold Spring Harbor Laboratory, N.Y. (2001); Ausubel, "Current Protocols in Molecular Biology", Green Publishing Associates and Wley Interscience, N.Y. (1989), or Higgins and Hames (Eds.) "Nucleic acid hybridization, a practical approach" IRL Press Oxford, Washington D.C., (1985). In one preferred embodiment, the hybridization is effected is under stringent conditions.

"Stringent hybridization conditions" refers to conditions which comprise, e.g. an overnight incubation at 65° C. in 4×SSC (600 mM NaCl, 60 mM sodium citrate) followed by washing at 65° C. in 0.1×SSC for one hour. Alternatively, hybridization conditions can comprise: an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. Said conditions for hybridization are also known by a person skilled in the art as "highly stringent conditions for hybridization". Also contemplated are nucleic acid molecules that hybridize to the nucleic acid molecules of the invention at lower stringency hybridization conditions ("low stringency conditions for hybridization"). Changes in the stringency of hybridization and signal detection are primarily accomplished through the manipulation of formamide concentration (lower percentages of formamide result in lowered stringency), salt conditions, or temperature. For example, lower stringency conditions include an overnight incubation at 50° C. in 4×SSC or an overnight incubation at 37° C. in a solution comprising 6×SSPE (20×SSPE=3M NaCl; 0.2M NaH$_2$PO$_4$; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve an even lower stringency, washes performed following stringent hybridization can be done at higher salt concentrations (e.g. 5×SSC). It is of note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Such modifications can generally be effected by the skilled person without further ado. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed). The embodiment recited herein above preferably refers to highly stringent conditions and alternatively to conditions of lower stringency.

Further to the above, the term "a nucleic acid molecule hybridizing under stringent conditions to the complementary strand of a nucleic acid molecule encoding the polypeptide of (a) or (b)" as recited in item (c) preferably refers to sequences which display a sequence identity of at least 70%, preferably of at least 80%, more preferred of at least 90%, even more preferred of at least 95% and most preferred of at least 97% with a nucleotide sequence as described above in items (a) or (b).

As stated herein above, preferred in accordance with the present invention are nucleic acid molecules which are capable of hybridizing to the nucleic acid molecules of the invention or parts thereof, under (highly) stringent hybridization conditions, i.e. which do not cross hybridize to nucleic acid molecules unrelated in nucleotide sequence. In accordance with item (c), above, nucleic acid molecules related but not identical in sequence with the nucleic acid molecules of items (a) and (b) are also encompassed by the invention. In addition, the invention comprises according to item (c) fragments of the nucleic acid molecule of (a) and (b). For all embodiments falling under item (c), it is essential in accordance with this embodiment, that the polypeptide encoded by this nucleic acid molecule has at least the two N-terminal methionine residues and retains or essentially retains the biological activity of the histone of (a) or (b).

Moreover, in a preferred embodiment the present invention also relates to a nucleic acid molecule the sequence of which is degenerate in comparison with the sequence of an above-described nucleic acid molecule of item (a) or (b). When used in accordance with the present invention the term "being degenerate as a result of the genetic code" means that due to the redundancy of the genetic code different nucleotide sequences code for the same amino acid.

While there are a number of affinity tags known in the art which are fused to polypeptides to allow for easier production and detection, these tags often have to be removed for use in therapeutic applications. In contrast to these affinity tags the present inventors have surprisingly found bis-met polypeptides that show the same biological properties as their natural counterparts and, therefore, the polypeptides of the invention may be used for therapeutic purposes. As the functionality of the polypeptides of the invention is not detectably altered, at least not with the tests employed by the inventors, removal of the methionine residues is not necessary. Furthermore, removal of the methionine residues does not occur during production. As outlined above, cleavage of the N-terminal methionine residue is largely dependent on the size of the second amino acid residue. As the polypeptides of the present invention contain as a second amino acid residue a further methionine, one effect observed is that only a low percentage, i.e. in the range of about 20%, of the two N-terminal methionine residues are cleaved off in *E. coli*. In the remaining about 80% of the cases, the two N-terminal methionine residues are not cleaved off. During production of the polypeptide of the invention in prokaryotes such as *E. coli* the ultimate N-terminal methionine may also be formylated. However, the inventors did not obtain any formylated products as tested by mass spectrometry. Also, cleavage of only one methionine residue could not be observed. Without wanting to be bound by theory it is assumed that cleavage of the first N-terminal methionine residues leads to quick removal of the second N-terminal methionine as well, thus resulting in the cleavage of both methione residues.

In that regard the bis-met histones of the invention offer the advantage of being easily detectable in the presence of the endogenous histone. For example, although the bis-met histones may not be separated from their endogenous counterpart by different modes of HPLC (RPC; SEC; IEX) or electrophoresis (SDS-PAGE, CE), the bis-met histone can easily be distinguished by electro-spray ionization (or tandem) mass spectrometry (ESI-MS) e.g. the same RP-HPLC fraction (see Examples). This enables the monitoring of pharmacokinetics of therapeutic histones during clinical trials without the necessity of using isotope-labelling or special antibodies against the drug of examination.

Furthermore, it has been surprisingly found that histones containing two methionine residues as their first and second N-terminal amino acid residue showed advantageous properties in recombinant production. Thus, the inventors found that a significant higher level of histone could be obtained after introduction of the two methionine residues. Although the yield in the bacterial cell post fermentation of the bis-met histone was not significantly higher, surprisingly the behavior of the bis-met histone was found significantly different in the first key step of the downstream processing. While the bis-met histone could eluted at the expected salinity the recombinant histone devoid of the additional methionine residues could not be eluted from the Macroprep High S column except at very high salinity and could not be further purified in an efficient way. Consequently the bis-met histone displays an exquisite behavior on the Macroprep High S column allowing an efficient and high yield purification process.

Accordingly, the present invention is based on the novel finding that the presence of two methionine residues at the N terminus of histones provides bis-met histones which offer the possibility of simple detection in the presence of endogenous histones and allows for an efficient recombinant protein production.

In a preferred embodiment the histone is selected from the group consisting of histone H1.0, H1.1, H1.2, H1.3, H1.4, H1.5 and H1t Testis.

The Swiss-Prot accession numbers for human histone H1 subtypes are: H1.0-P07305, H1.1-Q02539, H1.2-P16403, H1.3-P16402, H1.4-P10412, H1.5-Q14529 and H1t-P22492. The nucleic acid and amino acid sequences of human histone H1.2 are shown in SEQ ID NOs: 6 and 7. The nucleic acid and amino acid sequences of human histone H1.3 are shown in SEQ ID NOs: 8 and 9. The nucleic acid and amino acid sequences of human histone H1.4 are shown in SEQ ID NOs: 10 and 11. The nucleic acid and amino acid sequences of human histone H1.5 are shown in SEQ ID NOs: 12 and 13.

In another embodiment the invention provides a nucleic acid molecule which is complementary to the nucleic acid molecule of the invention.

Nucleic acid molecules are "complementary" if they naturally bind to each other under permissive salt and temperature conditions by base-pairing. For example, the sequence "A-G-T" binds to the complementary sequence "T-C-A". "Complementary" in accordance with the invention, refers to the complete base pairing of nucleotides over the entire length of the nucleic acid molecule of the invention. Thus, a nucleic acid molecule labeled with a detectable label not exactly complementary to the nucleic acid molecule of the invention will not give rise to a detectable signal, if appropriate hybridization and washing conditions are chosen. Such complementary nucleic acid molecule may, for example, be used as probes in Northern or Southern blot analysis of RNA or DNA preparations.

In another aspect, the present invention provides an anti-sense oligo- or polynucleotide of a nucleic acid molecule of the invention, wherein the oligonucleotide comprises the nucleotides being complementary to the nucleotide triplets encoding the two N-terminal methionine residues of the histone of the invention and has a minimal length of 10 nucleotides.

Said anti-sense oligonucleotides may, for example, be used as primers for sequencing assays or as probes in Northern or Southern blot analysis of RNA or DNA preparations. Anti-sense oligonucleotides of the present invention preferably comprise at least 10, preferably at least 15 such as at least 25 consecutive nucleotides. Anti-sense polynucleotides of the present invention more preferably comprise at least 100, more preferably at least 200, and most preferably at least 500 nucleotides in length.

Such a nucleic acid molecule may also be used, e.g., as a probe in RNase protection assays, or as an anti-sense probe to inhibit expression of the histones of the present invention. The person skilled in the art is familiar with the preparation and the use of said probes (see, e.g., Sambrook and Russel "Molecular Cloning, A Laboratory Manual", Cold Spring Harbor Laboratory, N.Y. (2001)).

In another alternative embodiment the invention provides a vector comprising the nucleic acid molecule of the invention. Preferably, the vector is a plasmid, cosmid, virus, bacteriophage or another vector used e.g. conventionally in genetic engineering. In a further embodiment the invention provides a vector comprising the complementary nucleic acid molecule or the anti-sense oligonucleotide of the invention.

The nucleic acid molecule of the present invention may be inserted into several commercially available vectors. Non-limiting examples include prokaryotic plasmid vectors, such as the pUC-series, pBluescript (Stratagene), the pET-series of expression vectors including the pETduet-vectors (Novagen) or pCRTOPO (Invitrogen) and vectors compatible with an expression in mammalian cells like pREP (Invitrogen), pcDNA3 (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, pLXIN, pSIR (Clontech), pIRES-EGFP (Clontech), pEAK-10 (Edge Biosystems) pTriEx-Hygro (Novagen) and pCINeo (Promega). Examples for plasmid vectors suitable for *Pichia pastoris* comprise e.g. the plasmids pAO815, pPIC9K and pPIC3.5K (all Invitrogen).

The nucleic acid molecule of the present invention referred to above may also be inserted into vectors such that a translational fusion with another nucleic acid molecule is generated. The other nucleic acid molecule may encode a protein which may e.g. increase the solubility and/or facilitate the purification of the fusion protein. Non-limiting examples include pET32, pET41, pET43. The vectors may also contain an additional expressible nucleic acid molecule coding for one or more chaperones to facilitate correct protein folding. Suitable bacterial expression hosts comprise e.g. strains derived from BL21 (such as BL21(DE3), BL21 (DE3)PlysS, BL21(DE3)RIL, BL21(DE3)PRARE) or ROSETTA®.

For vector modification techniques, see Sambrook et al., supra. Generally, vectors can contain one or more origin of replication (ori) and inheritance systems for cloning or expression, one or more markers for selection in the host, e.g., antibiotic resistance, and one or more expression cassettes. Suitable origins of replication (ori) include, for example, the Col E1, the SV40 viral and the M 13 origins of replication.

The coding sequences inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of the transcription (e.g., translation initiation codon, promoters, enhancers, and/or insulators), internal ribosomal entry sites (IRES) (Owens, Proc. Natl. Acad. Sci. USA 98 (2001), 1471-1476) and optionally poly-A signals ensuring termination of transcription and stabilization of the transcript. Additional regulatory elements may include transcriptional as well as translational enhancers, and/or naturally-associated or heterologous promoter regions. Preferably, the nucleic acid molecule of the invention is operatively linked to such expression control sequences allowing expression in prokaryotes or eukaryotic cells. The vector may further comprise nucleotide sequences encoding secretion signals as further regulatory elements. Such sequences are well known to the person skilled in the art. Furthermore, depending on the expression system used, leader sequences capable of directing the expressed polypeptide to a cellular compartment may be added to the coding sequence of the nucleic acid molecule of the invention. Such leader sequences are well known in the art.

Possible examples for regulatory elements ensuring the initiation of transcription comprise the cytomegalovirus (CMV) promoter, SV40-promoter, RSV-promoter (Rous sarcoma virus), the lacZ promoter, the gai10 promoter, human elongation factor 1α-promoter, CMV enhancer, CaM-kinase promoter, the *Autographa californica* multiple nuclear polyhedrosis virus (AcMNPV) polyhedral promoter or the SV40-enhancer. For the expression in prokaryotes, a multitude of promoters including, for example, the tac-lac-promoter, the lacUV5 or the trp promoter, has been described. Examples for further regulatory elements in prokaryotes and eukaryotic cells comprise transcription termination signals, such as SV40-poly-A site or the tk-poly-A site or the SV40, lacZ and AcMNPV polyhedral polyadenylation signals, downstream of the nucleic acid molecule.

Furthermore, it is preferred that the vector of the invention comprises a selectable marker. Examples of selectable markers include neomycin, ampicillin, and hygromycine, kanamycine resistance and the like. Specifically-designed vectors allow the shuttling of DNA between different hosts, such as bacteria-fungal cells or bacteria-animal cells (e.g. the GATEWAY® system available at Invitrogen).

An expression vector according to this invention is capable of directing the replication, and the expression, of the nucleic acid molecule and encoded polypeptide of this invention. Suitable expression vectors which comprise the described regulatory elements are known in the art such as Okayama-Berg cDNA expression vector pcDV1 (Pharmacia), pRc/CMV, pcDNA1, pcDNA3 (In-Vitrogene, as used, inter alia in the appended examples), pSPORT1 (GIBCO BRL) or pGEMHE (Promega), or prokaryotic expression vectors, such as lambda gt11, pJOE, the pBBR1-MCS-series, pJB861, pBSMuL, pBC2, pUCPKS, pTACT1 or, preferably, the pET vector (Novagen).

The nucleic acid molecules of the invention as described herein above may be designed for direct introduction or for introduction via liposomes, phage vectors or viral vectors (e.g. adenoviral, retroviral) into the cell. Additionally, baculoviral systems or systems based on Vaccinia Virus or Semliki Forest Virus can be used as eukaryotic expression system for the nucleic acid molecules of the invention.

A typical mammalian expression vector contains the promoter element, which mediates the initiation of transcription of mRNA, the protein coding sequence, and signals required for the termination of transcription and polyadenylation of the transcript. Moreover, elements such as origin of replication, drug resistance gene, regulators (as part of an inducible promoter) may also be included. The lac promoter is a typical inducible promoter, useful for prokaryotic cells, which can be induced using the lactose analogue isopropylthiol-b-D-galactoside. ("IPTG"). For recombinant expression and secretion, the nucleic acid molecule of interest may be ligated between e.g. the PelB leader signal, which directs the recombinant protein in the periplasm and the gene III in a phagemid called pHEN4 (described in Ghahroudi et al, 1997, FEBS Letters 414:521-526). Additional elements might include enhancers, Kozak sequences and intervening sequences flanked by donor and acceptor sites for RNA splicing. Highly efficient transcription can be achieved with the early and late promoters from SV40, the long terminal repeats (LTRs) from retroviruses, e.g., RSV, HTLVI, HIVI, and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells. Alternatively, the recombinant polypeptide can be expressed in stable cell lines that contain the gene construct integrated into a chromosome. The co-transfection with a selectable marker such as dhfr, gpt, neomycin, hygromycin allows the identification and isolation of the transfected cells. The transfected nucleic acid can also be amplified to express large amounts of the encoded polypeptide. The DHFR (dihydrofolate reductase) marker is useful to develop cell lines that carry several hundred or even several thousand copies of the gene of interest. Another useful selection marker is the enzyme glutamine synthase (GS) (Murphy et al. 1991, Biochem J. 227:277-279; Bebbington et al. 1992, Bio/Technology 10:169-175). Using these markers, the mammalian cells are grown in selective medium and the cells with the highest resistance are selected. As indicated above, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria.

The present invention in addition relates to a host genetically engineered with the nucleic acid molecule of the invention or with a vector of the invention. Said host may be produced by introducing said nucleic acid molecule or vector(s) into a host which upon its/their presence mediates the expression of the polypeptide of the invention.

The host may be any prokaryote or eukaryotic cell. Suitable prokaryotes/bacteria are those generally used for cloning like *E. coli* (e.g., *E. coli* strains BL21(DE3), HB101, DH5α, XL1 Blue, Y1090 and JM101), *Salmonella typhimurium, Serratia marcescens, Pseudomonas putida, Pseudomonas fluorescens, Streptomyces lividans, Lactococcus lactis, Mycobacterium smegmatis* or *Bacillus subtilis*. A suitable eukaryotic host may be an animal cell such as CHO, COS, 293 and Bowes melanoma cells, an amphibian cell, a fish cell, an insect cell such as *Drosophila* S2 and *Spodoptera* Sf9 cells, a fungal cell, a plant cell, transgenic non-human animals or transgenic plants.

In a preferred embodiment of the present invention the host is a bacterium, a yeast cell, an insect cell, a fungal cell, a mammalian cell or a plant cell. Appropriate culture mediums and conditions for the above-described host cells are well known in the art.

In a preferred embodiment the host to be genetically engineered with the nucleic acid molecule or the vector of the invention is *E. coli.*, for example strains derived from BL21 (such as BL21(DE3), BL21(DE3)PlysS, BL21(DE3) RIL, BL21(DE3)PRARE) or ROSETTA®.

In a further embodiment the present invention also relates to a process for producing bacteria or eukaryotic cells capable of expressing a polypeptide of the invention, the process comprising genetically engineering bacteria or eukaryotic cells with the vector of the present invention. The term "genetic engineering" refers to the process of bringing into a cell genetic information or modifying the genetic information of a cell. This is generally accomplished by transfecting or transforming a host cell with a nucleic acid molecule. Introduction of a construct into the host cell can be effected by calcium phosphate transfection, DEAE-dextran mediated transfection, cationic lipid-mediated transfection, electroporation, transduction, infection or other methods. Such methods are described in many standard laboratory manuals, such as Sambrook et al., loc. cit. supra. Said nucleic acid molecule introduced into the host cell comprises an open reading frame encoding the polypeptide of the present invention.

In an additional embodiment, the present invention relates to a method of producing a polypeptide of the invention comprising culturing the host of the invention under suitable conditions and isolating the polypeptide of the invention produced from said host or culture.

A large number of suitable methods exist in the art to produce polypeptides in appropriate hosts. If the host is a unicellular organism such as a prokaryote, a mammalian or insect cell, the person skilled in the art can revert to a variety of culture conditions. Conveniently, the produced protein is harvested from the culture medium, lysates of the cultured organisms or from isolated (biological) membranes by established techniques. In the case of a multicellular organism, the host may be a cell which is part of or derived from a part of the organism, for example said host cell may be the harvestable part of a plant. A preferred method involves the recombinant production of protein in hosts as indicated above. For example, nucleic acid sequences comprising the nucleic acid molecule according to the invention can be synthesized by PCR and inserted into an expression vector. Subsequently a suitable host may be transformed with the expression vector. Thereafter, the host is cultured to produce the desired polypeptide, which is isolated and purified. Such methods are well known in the art (see, e.g., Sambrook et al., supra).

An alternative method for producing the polypeptide of the invention is in vitro translation of mRNA. Suitable cell-free expression systems for use in accordance with the present invention include rabbit reticulocyte lysate, wheat germ extract, canine pancreatic microsomal membranes, E. coli S30 extract, and coupled transcription/translation systems such as the TNT-system (Promega). These systems allow the expression of recombinant polypeptides upon the addition of cloning vectors, DNA fragments, or RNA sequences containing coding regions and appropriate promoter elements.

In addition to recombinant production, the polypeptide (protein), fragments of the protein or the fusion protein of the invention may be produced synthetically, e.g. by direct peptide synthesis using solid-phase techniques (cf Stewart et al. (1969) Solid Phase Peptide Synthesis; Freeman Co, San Francisco; Merrifield, J. Am. Chem. Soc. 85 (1963), 2149-2154).

Synthetic protein synthesis may be performed using manual techniques or by automation. Automated synthesis may be achieved, for example, using the Applied Biosystems 431A Peptide Synthesizer (Perkin Elmer, Foster City Calif.) in accordance with the instructions provided by the manufacturer. Various fragments may be chemically synthesized separately and combined using chemical methods to produce the full length molecule. As indicated above, chemical synthesis, such as the solid phase procedure described by Houghton (Proc. Natl. Acad. Sci., 1985, 82: 5131) can be used. Furthermore, the polypeptide (protein), fragments of the protein or the fusion protein of the invention may be produced semi-synthetically, for example by a combination of recombinant and synthetic production. All polypeptides (proteins) having two methionine residues as the first and second N-terminal amino acid residues linked via a peptide bond to (a) a mature eukaryotic histone; (b) a mature eukaryotic polypeptide having at least 80% sequence identity to a mature eukaryotic histone and essentially retaining its biological activity; or (c) any other polypeptide of the invention as described above as well as fragments of the polypeptide (protein) and fusion proteins fall within the scope of the present invention irrespective of the production method used to obtain them. This is because the amino acid sequence of all these proteins is (also) encoded by the nucleic acid molecule of the invention.

Protein isolation and purification can be achieved by any one of several known techniques; for example and without limitation, ion exchange chromatography, gel filtration chromatography, affinity chromatography, high pressure liquid chromatography (HPLC), reversed phase HPLC, hydrophobic interaction chromatography and preparative disc gel electrophoresis. Protein isolation/purification techniques may require modification of the polypeptides of the present invention using conventional methods. For example, a histidine tag can be further added to the protein to allow purification on a nickel column. Other modifications may cause higher or lower activity, permit higher levels of protein production, or simplify purification of the protein.

In an alternative embodiment the invention provides a polypeptide encoded by the nucleic acid molecule of the invention or produced by the method of the invention.

The invention also provides a composition comprising the nucleic acid molecule or the vector or the host or the polypeptide of the present invention. Optionally, the antibody, aptamer or phage of the invention described further below is also contained in said compositions.

The term "composition", as used in accordance with the present invention, relates to a composition which comprises at least one of the recited compounds. It may, optionally, comprises further molecules capable of altering the characteristics of the compounds of the invention thereby, for example, suppressing, stabilizing, blocking, modulating and/or activating their function. The composition may be in solid, liquid or gaseous form and may be, inter alia, in the form of (a) powder(s), (a) tablet(s), (a) solution(s) or (an) aerosol(s).

In a preferred embodiment the composition of the invention further comprises the mature eukaryotic histone.

Preferably, such a composition comprises the polypeptide of the invention (bis-met histone) in a mixture with the mature eukaryotic histone. Therefore, the composition may comprise a mixture of histones containing two methionine residues at the N terminus and histones being devoid of both methionine residues. Preferably, the mixture is in the range of 90% of the polypeptide of the invention to 10% mature eukaryotic histone. More preferred the mixture is in the range of 80% to 20%, more preferably 70% to 30%. Even more preferred are ranges of 50% to 50%, 30% to 70% or 20 to 80% of the mixture. Most preferably the mixture is in the range of 10% of the polypeptide of the invention to 90% of the mature eukaryotic histone. Such a mixture may result from the partial cleavage of the methionine from the bis-met histone due to insufficient activity of the methionine aminopeptidase of the host organism. Alternatively, the mature eukaryotic histone may be added to the bis-met histone of the invention to obtain said mixture. Preferably, the histones in the mixture are of the same subtype such as H1 or H2A.

In another preferred embodiment the composition is a pharmaceutical composition optionally further comprising a pharmaceutically acceptable carrier and/or diluent.

In accordance with the present invention, the term "pharmaceutical composition" relates to a composition for administration to a patient, preferably a human patient. The pharmaceutical composition of the invention comprises the compounds recited above. The pharmaceutical composition of the present invention may, optionally and additionally, comprise a pharmaceutically acceptable carrier. By "pharmaceutically acceptable carrier" is meant a non-toxic solid, semisolid or liquid filler, diluent, encapsulating material or formulation auxiliary of any type. Examples of suitable pharmaceutical carriers are well known in the art and include sodiumchloride solutions, phosphate buffered sodiumchloride solutions, water, emulsions, such as oil/water emulsions, various types of wetting agents, sterile solutions, organic solvents including DMSO etc. Preferably the carrier is a parenteral carrier, more preferably a solution that is isotonic with the blood of the recipient. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The term "parenteral" as used herein refers to modes of administration which include intravenous, intramuscular, intraperitoneal, intrasternal, subcutaneous and intraarticular injection and infusion.

Compositions comprising such carriers can be formulated by well-known conventional methods. Generally, the formulations are prepared by contacting the components of the pharmaceutical composition uniformly and intimately with liquid carriers or finely divided solid carriers or both. Then, if necessary, the product is shaped into the desired formulation.

These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgment of the ordinary clinician or physician. Generally, the regimen as a regular administration of the pharmaceutical composition should be in the range of 1 µg to 20 g units per day. However, a more preferred dosage might be in the range of 0.01 mg to 100 mg, even more preferably 0.01 mg to 50 mg and most preferably 0.01 mg to 10 mg per day.

The components of the pharmaceutical composition to be used for therapeutic administration must be sterile. Sterility is readily accomplished by filtration through sterile filtration membranes (e.g., 0.2 micron membranes).

The components of the pharmaceutical composition ordinarily will be stored in unit or, multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic Water-for-Injection.

Preservatives and other additives may also be present such as, for example, antimicrobials, antioxidants, chelating agents, and inert gases and the like. Furthermore, the pharmaceutical composition may comprise further agents depending on the intended use of the pharmaceutical composition.

The pharmaceutical composition may be particularly useful for the treatment of diseases, preferably diseases selected from those described herein above, including for example cancer, thrombocytopenia, infections such as bacterial, viral or fungal infections, autoimmune diseases such as systemic lupus erythematodes (SLE) or rheumatoid arthritis, ulcerative colitis or diseases with amyloid-like fibrils such as Alzheimer's disease (AD) and Parkinson's disease (PD), Leishmaniasis, certain forms of myopathy or cardiovascular disorders related to thrombotic events.

Cancer, in accordance with the present invention refers to a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system).

Thrombocytopenia, in accordance with the present invention refers to the presence of relatively few platelets in blood, whereas a normal platelet count generally ranges from 140,000 to 400,000 per $mm^3$.

An infection in accordance with the present invention is the detrimental colonization of a host organism by a foreign species. In an infection, the infecting organism seeks to utilize the host's resources in order to multiply (usually at the expense of the host). The host's response to infection is inflammation.

Bacterial infections, in accordance with the present invention include but are not limited to Bacterial Meningitis, Cholera, Diphtheria, Listeriosis, Pertussis (Whooping Cough), Pneumococcal pneumonia, Salmonellosis, Tetanus, Typhus, Tuberculosis or Urinary Tract Infections.

Viral infections, in accordance with the present invention include but are not limited to Mononucleosis, AIDS, Chickenpox, Common cold, Cytomegalovirus Infection, Dengue fever, Ebola Haemorrhagic fever, Hand-foot and mouth disease, Hepatitis, Influenza, Mumps, Poliomyelitis, Rabies, Smallpox, Viral encephalitis, Viral gastroenteritis, Viral encephalitis, Viral meningitis, Viral pneumonia or Yellow fever.

Fungal infections in accordance with the present invention include but are not limited to Aspergillosis, Blastomycosis, Candidiasis, Coccidioidomycosis, Cryptococcosis, Histoplasmosis, Histoplasmosis or Tinea pedis.

Autoimmune diseases, in accordance with the present invention refer to diseases which arise from an overactive immune response of the body against substances and tissues normally present in the body. Autoimmune diseases are well known to the person skilled in the art and include, but are not limited to Lupus erythematosus, Acute disseminated encephalomyelitis, Aplastic anemia, Autoimmune hepatitis, Diabetes mellitus, Multiple sclerosis, Optic neuritis or Rheumatoid arthritis.

Lupus erythematosus in accordance with the present invention refers to a chronic (long-lasting) autoimmune disease wherein the immune system becomes hyperactive and attacks normal tissue. This attack results in inflammation and brings about symptoms. Lupus erythematosus is a "Non-organ-specific" type of autoimmune disease.

Rheumatoid arthritis in accordance with the present invention is an autoimmune disorder that causes the body's immune system to attack the bone joints.

Ulcerative colitis in accordance with the present invention is a form of inflammatory bowel disease (IBD). Ulcerative colitis is a form of colitis, a disease of the intestine, specifically the large intestine or colon, that includes characteristic ulcers, or open sores, in the colon. The main symptom of active disease is usually diarrhea mixed with blood, of gradual onset. Ulcerative colitis is, however, a systemic disease that affects many parts of the body outside the intestine.

Diseases with amyloid-like fibrils in accordance with the present invention are diseases which share as a common feature that the normally soluble peptide amyloid-beta or the protein alpha-synuclein aggregates into an ordered fibrillar structure typically resulting in increased oxidative injury, excitotoxicity and altered cell cycle. Diseases with amyloid-like fibrils include but are not limited to Alzheimer's disease (AD) and Parkinson's disease (PD).

Alzheimer's disease is a neurodegenerative disease characterized by progressive cognitive deterioration together with declining activities of daily living and neuropsychiatric symptoms or behavioral changes. It is the most common type of dementia.

Parkinson's disease is a degenerative disorder of the central nervous system that often impairs the sufferer's motor skills and speech.

Leishmaniasis is a trypanosomal disease caused by species of *Leishmania*, a parasitic organism of the genus of trypanosome protozoa. Leishmaniasis is transmitted by the bite of certain species of sand fly and symptoms are skin sores as well as fever, damage to the spleen and liver, and anaemia.

Myopathies are neuromuscular diseases in which the muscle fibers do not function, resulting in muscular weakness. Several classes of myopathy are known and include but are not limited to for example muscular dystrophies, congenital myopathies, mitochondrial myopathies or inflammatory myopathies.

Cardiovascular disorders related to thrombotic events, in accordance with the present invention, relate to disorders including, but not limited to, deep vein thrombosis or myocardial infarction. Particularly preferred are cardiovascular disorders related to thrombotic events mediated by γ-thrombin.

In another preferred embodiment the composition of the invention is a diagnostic composition.

In accordance with the present invention, the term "diagnostic composition" relates to compositions for diagnosing individual patients for their potential response to or curability by the pharmaceutical compositions of the invention. The diagnostic composition of the invention comprises the compounds recited above. The diagnostic composition may further comprise appropriate buffer(s), and enzymes such as reverse transcriptase, thermostable polymerases etc. The diagnostic compositions may be packaged in a container or a plurality of containers.

The invention also provides a method of treating and/or preventing a disease selected from cancer, thrombocytopenia, infections such as bacterial, viral or fungal infections, autoimmune diseases such as systemic lupus erythematosus (SLE) or rheumatoid arthritis, ulcerative colitis or diseases with amyloid-like fibrils such as Alzheimer's disease (AD) and Parkinson's disease (PD), myopathy or cardiovascular disorders related to thrombotic events comprising administering the pharmaceutical composition of the invention to a subject in need thereof.

The invention also provides the use of the nucleic acid molecule or the vector or the non-human host or the polypeptide of the invention for the preparation of a composition for therapeutic and/or diagnostic purposes.

In a preferred embodiment the therapeutic purpose is the treatment of cancer, thrombocytopenia, infections such as bacterial, viral or fungal infections, autoimmune diseases such as systemic lupus erythematodes (SLE) or rheumatoid arthritis, ulcerative colitis or diseases with amyloid-like fibrils such as Alzheimer's disease (AD) and Parkinson's disease (PD), myopathy or cardiovascular disorders related to thrombotic events.

In a further embodiment the invention provides an antibody or aptamer or phage that specifically binds to the nucleic acid molecule or the polypeptide of the invention but does not bind to the corresponding mature eukaryotic histone.

Said antibody may be a monoclonal or a polyclonal antibody.

The term "antibody" includes monoclonal antibodies, polyclonal antibodies, single chain antibodies, or fragments thereof that specifically bind said peptide or polypeptide, also including bispecific antibodies, synthetic antibodies, antibody fragments, such as Fab, a F(ab$_2$)', Fv or scFv fragments etc., or a chemically modified derivative of any of these. Monoclonal antibodies can be prepared, for example, by the techniques as originally described in Kohler and Milstein, Nature 256 (1975), 495, and Galfre, Meth. Enzymol. 73 (1981), 3, which comprise the fusion of mouse myeloma cells to spleen cells derived from immunized mammals with modifications developed by the art. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to an epitope of the peptide or polypeptide of the invention (Schier, Human Antibodies Hybridomas 7 (1996), 97-105; Malmborg, J. Immunol. Methods 183 (1995), 7-13). The production of chimeric antibodies is described, for example, in WO89/09622. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735. Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning: A Laboratory Manual, Cold Spring Harbor Laboratory, Cold Spring Harbor, N.Y., 1989.

The term "monoclonal" or "polyclonal antibody" (see Harlow and Lane, (1988), loc. cit.) also relates to derivatives of said antibodies which retain or essentially retain their binding specificity. Whereas particularly preferred embodiments of said derivatives are specified further herein below, other preferred derivatives of such antibodies are chimeric antibodies comprising, for example, a mouse or rat variable region and a human constant region.

The term "scFv fragment" (single-chain Fv fragment) is well understood in the art and preferred due to its small size and the possibility to recombinantly produce such fragments.

Preferably, the antibody, aptamer, fragment or derivative thereof according to the invention specifically binds the target protein, polypeptide or fragment or epitope thereof whose presence or absence is to be monitored.

The term "specifically binds" used in accordance with the present invention means that the antibody etc. does not or essentially does not cross-react with polypeptides of similar structures or with the mature eukaryotic polypeptide not having the N-terminal two methionine residues. Cross-reactivity of a panel of antibodies etc. under investigation may be tested, for example, by assessing binding of said panel of antibodies etc. under conventional conditions (see, e.g., Harlow and Lane, (1988), loc. cit.) to the polypeptide of interest as well as to a number of more or less (structurally and/or functionally) closely related polypeptides. Only those antibodies that bind to the polypeptide/protein of interest but do not or do not essentially bind to any of the other polypeptides which are preferably expressed by the same tissue as the polypeptide of interest, are considered specific for the polypeptide/protein of interest and selected for further studies in accordance with the method of the invention.

In a particularly preferred embodiment of the method of the invention, said antibody or antibody binding portion is or is derived from a human antibody or a humanized antibody. The term "humanized antibody" means, in accordance with the present invention, an antibody of non-human origin, where at least one complementarity determining region (CDR) in the variable regions such as the CDR3 and preferably all 6 CDRs have been replaced by CDRs of an antibody of human origin having a desired specificity. Optionally, the non-human constant region(s) of the antibody has/have been replaced by (a) constant region(s) of a human antibody. Methods for the production of humanized antibodies are described in, e.g., EP-A1 0 239 400 and WO90/07861.

Aptamers are DNA or RNA molecules that have been selected from random pools based on their ability to bind other molecules. Aptamers have been selected which bind nucleic acid, proteins, small organic compounds, and even entire organisms. A database of aptamers is maintained at http://aptamer.icmb.utexas.edu/.

More specifically, aptamers can be classified as DNA or RNA aptamers or peptide aptamers. Whereas the former consist of (usually short) strands of oligonucleotides, the latter consist of a short variable peptide domain, attached at both ends to a protein scaffold.

Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms.

Peptide aptamers are proteins that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range). The variable loop length is typically comprised of 10 to 20 amino acids, and the scaffold may be any protein which have good solubility properties. Currently, the bacterial protein Thioredoxin-A is the most used scaffold protein, the variable loop being inserted within the reducing active site, which is a -Cys-Gly-Pro-Cys-loop in the wild protein, the two cysteines lateral chains being able to form a disulfide bridge. Peptide aptamer selection can be made using different systems, but the most used is currently the yeast two-hybrid system.

Aptamers offer the utility for biotechnological and therapeutic applications as they offer molecular recognition properties that rival those of the commonly used biomolecules, in particular antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications.

Non-modified aptamers are cleared rapidly from the bloodstream, with a half-life of minutes to hours, mainly due to nuclease degradation and clearance from the body by the kidneys, a result of the aptamer's inherently low molecular weight. Unmodified aptamer applications currently focus on treating transient conditions such as blood clotting, or treating organs such as the eye where local delivery is possible. This rapid clearance can be an advantage in applications such as in vivo diagnostic imaging. Several modifications, such as 2'-fluorine-substituted pyrimidines, polyethylene glycol (PEG) linkage, etc. are available to scientists with which the half-life of aptamers easily can be increased to the day or even week time scale.

Phages in accordance with the present invention refer to recombinant phages and are well known in the art and are described, for example, in Griffiths, A. D. et al.: EMBO J. 1994, 13:3245. The phage may carry immunoglobuline fragments or derivatives with a desired binding specificity for the polypeptide of the invention as a fusion protein on their surface, wherein the fusion partner is a surface molecule of the phage.

In a preferred embodiment of the method of the invention said antibody or aptamer or phage is detectably labeled. Whereas the aptamers are preferably radioactively labeled with $^3$H or $^{32}$P or with a fluorescent marker such as described above, the phage or antibody may e.g. be labeled in a corresponding manner (with $^{131}$I as the preferred radioactive label) or be labeled with a tag such as His-tag, FLAG-tag or myc-tag.

In an alternative embodiment the invention provides a diagnostic composition comprising said antibody, aptamer and/or phage. Said composition may further comprise appropriate buffer(s), and enzymes such as reverse transcriptase, thermostable polymerases etc.

Said diagnostic composition may be used to test for the presence of the polypeptide of the invention in, e.g. an immuno-assay using the antibody of the invention. The term "immuno-assay", as used herein, comprises methods like, e.g., immuno-precipitation, immuno-blotting, ELISA, RIA, indirect immunofluorescence experiments, and the like. Such techniques are well known in the art and are described, e.g. in Harlow and Lane, supra.

In an alternative embodiment the invention provides a method for testing for the presence of the nucleic acid molecule or the polypeptide of the invention comprising assaying a sample obtained from a subject for the presence of said nucleic acid molecule or polypeptide.

Methods for testing a sample for the presence of the nucleic acid molecule of the invention comprise, but are not limited to, nucleic acid amplification, sequencing or hybridization assays.

Examples for nucleic acid amplification assays and means to perform such include without limitation PCR, (including nested PCR, RT-PCR, PCR extension assays, Nucleic Acid Sequence Base Amplification (NASBA), single-strand confirmation polymorphism (SSCP) PCR), amplification refractory mutation systems (ARMS™) and amplification refractory mutation system linear extension (ALEX™) assays. Details of such methods can be found in art, see, for example, Newton et al., Nucleic Acids Res. 17 (1989) 2503-2516; Agrawal (Ed.), "Protocols for Oligonucleotides and Analogs: Synthesis and Properties (Methods in Molecular Biology, 20)", Humana Press, 1993; Haque et al., Diagn. Mol. Pathol. 7 (1998) 248-252; Innis et al. (Ed.), "PCR Applications: Protocols for Functional Genomics", Academic Press, 1999; Chen and Janes (Ed.), "PCR Cloning Protocols: From Molecular Cloning to Genetic", 2nd edition, Humana Press, 2002; Pissard et al., Clin. Chem. 48 (2002) 769-772; Steemers et al., Nature Meth. 3 (2006) 31-33; Kakavas et al., J. Clin. Lab. Anal. 20 (2006) 1-7.

Examples for sequencing assays comprise without limitation approaches of sequence analysis by direct sequencing, fluorescent SSCP in an automated DNA sequencer and Pyrosequencing. These procedures are common in the art, see e.g. Adams et al. (Ed.), "Automated DNA Sequencing and Analysis", Academic Press, 1994; Alphey, "DNA Sequencing: From Experimental Methods to Bioinformatics", Springer Verlag Publishing, 1997; Ramon et al., J. Transl. Med. 1 (2003) 9; Meng et al., J. Clin. Endocrinol. Metab. 90 (2005) 3419-3422.

Examples for hybridization assays comprise without limitation Northern and Southern blot assays, heteroduplex analysis, detection of mutations by sequence specific oligonucleotide hybridization, allele-specific oligonucleotide hybridization on DNA chips, assays based on ILLUMINA® technology, assays based on the BEADARRAY®. technology, see, for example, Barnes et al., Nucleic Acids Res. 33 (2005) 5914-5923; Fan et al., Biotechniques 39 (2005) 583-588; Shen et al., Mutat. Res.-Fund. Mol. M. 573 (2005) 70-82; Steemers and Gunderson, Pharmacogenomics, 6 (2005) 777-782.

Examples for assays based on protein detection include without limitation method steps such as ion exchange chromatography, gel filtration chromatography, affinity chromatography, hydrophobic interaction chromatography, reversed phase HPLC, disc gel electrophoresis, capillary electrophoresis, Western blot analysis, immunoprecipitation, amino acid sequencing, spectroscopic methods (UV, CD; IR, Fluoreszenz) and mass spectrometry (e.g. MS-QTOF), see, for example, Soejima and Koda, Transfusion 45 (2005) 1934-1939; Yeh et al., Anesth. Analg. 101 (2005) 1401-1406; Chou et al., Am. J. Clin. Pathol. 124 (2005) 330-338.

The above described assays are known in the art, e.g. from standard text books such as Lottspeich, Engel "Bioanalytik" Spektrum Akademischer Verlag (2006); Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989); Higgins and Hames (Eds.) "Nucleic acid hybridization, a practical approach" IRL Press Oxford, Washington D.C., (1985); Nollau et al, Clin. Chem. 43 (1997), 1114-1128; The use of some of the recited assays is described in the appended examples.

In another preferred embodiment of the method of the invention said sample is blood, serum, plasma, fetal tissue, saliva, urine, mucosal tissue, mucus, vaginal tissue, fetal tissue obtained from the vagina, skin, hair, hair follicle or another human tissue. Preferably, the sample is blood, serum, plasma, saliva, urine, mucosal tissue, mucus.

The invention also relates to a Kit comprising the nucleic acid molecule, the vector, the non-human host, the polypeptide or the antibody, aptamer and/or phage of the invention in one or more containers.

The figures show:

FIG. 1: Schematic overview of the purification procedure

Figure 2:

FIG. 2. QTOF Mass spectrum of the B1, M-H1A-P02 clinical batch

Figure 3:
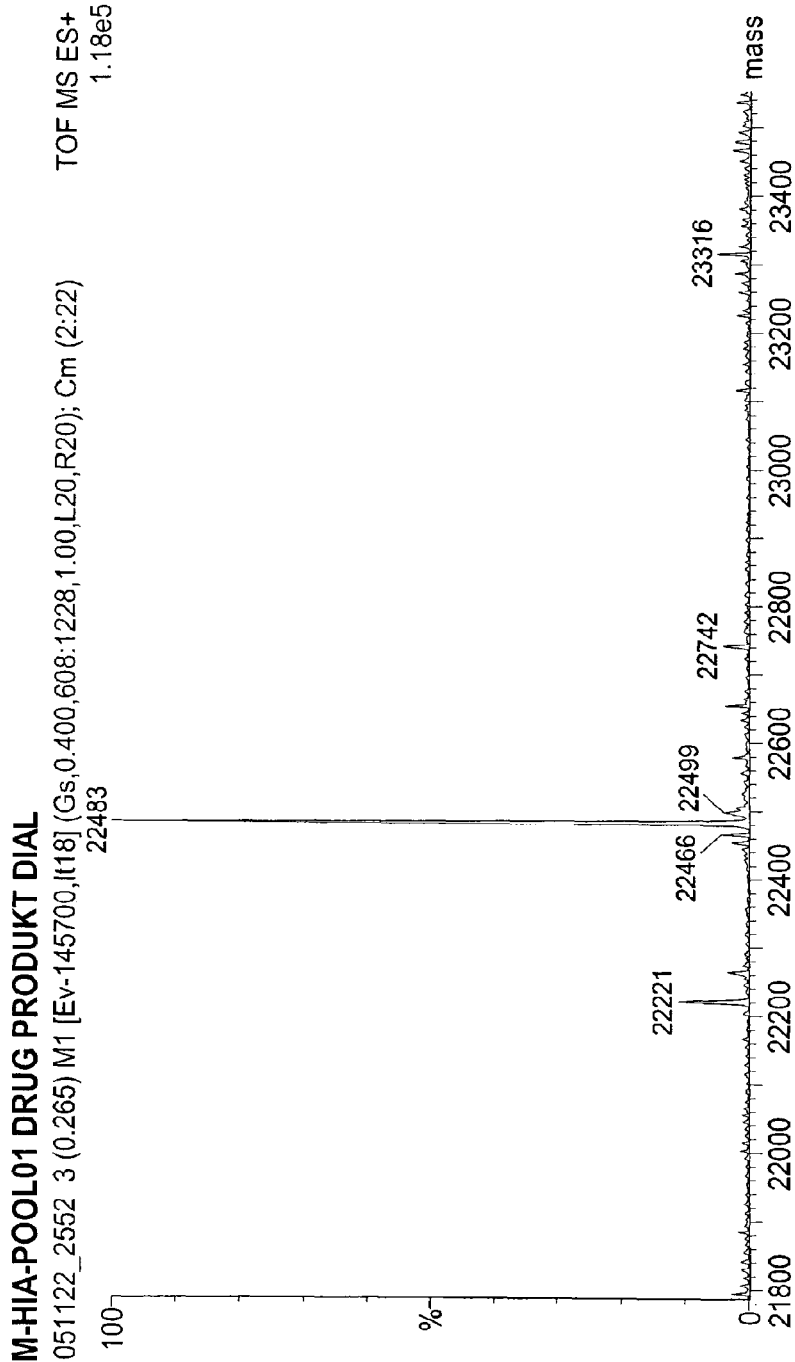

FIG. 3: QTOF Mass spectrum of the B2, M-H1A-Pool01 clinical batch

The invention will now be described by reference to the following examples which are merely illustrative and are not to be construed as a limitation of scope of the present invention.

EXAMPLE 1

Cloning of hH1.3 Constructs

Construction of Plasmid Vector pEGT1-rH1.3S1

As shown in SEQ ID NO: 1, histones displaying a strong positive charge resulting from a very high content of lysine residues. As the codon usage for lysine differs strongly between *Escherichia coli* and human, a codon optimization was performed in order to adapt the human histone H1.3 sequence to the codon usage of *E. coli*.

A synthetic gene was produced whose sequence is provided as SEQ ID NO: 2. The artificial sequence was flanked with two restriction sites, namely BspH1 and BamH1, to allow the subsequent introduction into pEGT1 expression vector. The translation initiation codon ATG was incorporated into a Nco1 restriction site CCATGG. The initial ATG was doubled which provides a BspH1 site TCATGA whose cohesive end CATG is compatible with Nco1. Thus, a second methionine residue was incorporated after the first one. An additional BamH1 site GGATCC was introduced after the termination codon TAA. The amino acid sequence encoded by this artificial gene is given in SEQ ID NO: 3.

The optimised gene was excised from its plasmid by digestion with BspH1 and BamH1 and inserted into pEGT1 expression vector linearized by NCO1 and BamH1 according to standard protocols to yield plasmid pEGT1-rH13S1.

The ligated vector pEGT1-rH13S1 was introduced into electrocompetent *E. coli* strain BL21[DE3] by electroporation using standard protocol and the transformed cells were selected on LB plate supplemented with kanamycine. One clone was selected and the sequence of the insert encoding for the histone was verified for its perfect match with SEQ ID NO: 2.

Construction of Plasmid Vector pEGT1-rH1.3S2

In order to suppress the insertion of a second methionine in the rH13S1 construct, a second synthetic gene was used. The second original codon TCC encoding for a Serine was changed into AGC also encoding for Serine to ensure compatibility with the BspH1 site. The DNA sequence is provided as SEQ ID NO: 4 and the recombinant protein encoded by this artificial gene is provided as SEQ ID NO: 5. The same cloning strategy as outlined above for pEGT1-rH13S1 was employed since the artificial gene of SEQ ID NO: 4 was flanked with the BspH1 restriction site TCATGA at the initiator codon and BamH1 CCATGG one base pair post terminator codon.

The optimised gene was excised from its plasmid by digestion with BspH1 and BamH1 and inserted into pEGT1 expression vector linearised by NCO1 and BamH1 according to standard protocols to yield plasmid pEGT1-rH13S2.

The ligated vector pEGT1-rH13S2 was introduced into electrocompetent *E. coli* strain BL21[DE3] by electroporation using standard protocol and the transformed cells were selected on LB plate supplemented with kanamycine. One clone was selected and the sequence of the insert encoding for the histone was verified for its perfect match with SEQ ID NO: 4.

EXAMPLE 2

Recombinant Production of Histone H1.3

The Strain

The bacterium used in the preparation of rh1.3S is a recombinant strain of *Escherichia coli* BL21 (DE3)/pEGT1/H1.3S. The constructions were used to transform BL21 (DE3) strain of *E. coli*. Three clones were selected to perform an expression screening and one clone was selected to do a pre-Master Seed (Pre-MS-05L23-H1B).

A Master Seed (MS-06D05-H1B) has been produced using the Pre-MS-05L23-H1B and a Working Seed (WS-06D06-H1B) has been produced using the Master Seed.

Seed Culture

Two 2-liters shake-flasks containing each 500 ml of YES medium (30 g/l yeast extract, 5 g/l NaCl) are inoculated each with 100 μl of the Working Seed (WS-06D06-H1B). The culture is incubated at 37° C. with an agitation of 270 rpm for 5 h00 (+/−0.5 hour) to reach an O.D (600 nm) of more than 1.5.

Fermentation

A 100-liters fermentor is prepared with 100 liters of NRJ18 medium. The fermentor is sterilised for 30 minutes at 123° C. After sterilisation and before inoculation, 50 ml of SAG 471 (antifoam) are added aseptically. The fermenter is inoculated with the seed culture in order to reach a theoretical initial optical density at 600 nm of $8.75 \times 10^{-7}$.

The calculated inoculum volume is added to a transfer bottle containing 500 ml of YES medium.

Fermentation is performed over-night at 37° C. During the fermentation process, pH is maintained at pH 7.0±0.2 by periodic addition of NaOH 4 M and $HNO_3$ 2.24M. Dissolved oxygen is feedback regulated on the agitation at 30%.

When the culture reaches an $OD_{600}$ between 15 and 20, the culture is induced with a solution of 1 mM IPTG (23.8 g dissolved in 500 ml of highly purified water).

After 1 h30 of induction, $OD_{600}$ is more than 24 and the fermentor is cooled down below 16° C. pH regulation is maintained at 7.0±0.2. Other parameters are kept constant during cooling except the pressure which is decreased down to 300 mbars and the agitation down to 200 rpm.

When medium temperature is below 16° C., the culture volume is estimated. The complete culture is centrifuged with 2 Beckman Centrifuges JA10 equipped with JLA 8.1000 rotor (±6 L/centrifuge): 5200 RPM-4° C.-20 minutes.

Cell pellets are harvested and stored progressively at −20° C. during the centrifugation step.

Cell Disruption in a High Pressure Homogenizer

The day before the cell disruption, the concentrated cells corresponding to 100 liters of culture are thawed at room temperature.

The day of the disruption, the cell pellets are diluted at 250 g/l in 20 mM $Na_2HPO_4.12H_2O$ pH 7.0 and the temperature of the suspension is increased to 30° C.

The suspension is then homogenised in a Heidolph R2R2100 propeller. The cells are then lysed in a high pressure homogenizer PONY (800 bars). The cell suspension is treated twice through the cell homogenizer.

EXAMPLE 3

Protein Purification

All steps of purification are performed on total volume of fermentor (i.e. 100 l).

1. Precipitation with 2.5% Perchloric Acid and 8 M Urea Extraction

To the harvested cell mass ⅐ of volume of $HClO_4$ 20% (final concentration: 2.5%) is added. The suspension is homogenised prior to a third cycle in the Pony homogeniser at 250 bars. The solution is kept under gentle agitation for one hour at room temperature. Then, the suspension is centrifuged for 15 minutes (12,200 g-7,000 rpm, 4° C.). The supernatant is collected, the pH adjusted at 4.0±0.1 with 10M NaOH and filtered through a 0.45/0.22 μm Sartopore 2 membrane (2000 cm²) into a sterile bag.

Urea is added to obtain an 8 M concentration in a double final volume, the volume being adjusted with 20 mM $Na_2HPO_4$ pH 7.0 buffer. The solution is kept overnight under gentle agitation at room temperature. Then, the pH is adjusted at 4.0±0.1 with 37% HCl or 10M NaOH.

2. Q Sepharose Fast Flow Anion Exchange Chromatography (QSFF)—Negative Mode

The aim of this step is a reduction of the Endotoxin and DNA content. Anion exchange chromatography is conducted with Q Sepharose Fast Flow (Amersham Biosciences cat. n° 17-0510-05) packed in a Moduline 350/500 column (Millipore BioProcess Division cat n° 86351211).

The column is packed in highly purified water at an eluent flow rate of 120 cm/h (115.4 l/h). The dimensions of the packed column bed are: diameter 25 cm, cross-sectional area=961 cm², bed=18 cm, packed volume=17.314±0.962 l. The column is sanitised with 1.5 to 2.5 column volume (CV) of 1M NaOH+2M NaCl with a contact time of 2 hours at a flow rate of 96.2 l/h (100 cm/h-1603 ml/min).

All the chromatographic steps are performed at a linear flow rate of approximately 100 cm/h (±96.2 l/h). The pH is stabilised with 1 to 2 CV of 50 mM Ammonium acetate+1M NaCl pH 4.0. The column is then equilibrated with 3.5 to 5 CV of 50 mM Ammonium acetate+8M urea pH 4.0.

The solution from urea extraction (see section 1) is diluted about 1.5 times with 50 mM Ammonium acetate+8M urea pH 4.0 in order to obtain a conductivity lower than 10 mS/cm. Only 8 CV of urea extraction solution (before dilution) are loaded at the same time. The H1 protein is collected in the flow through, the equilibration-elution being performed with 1.5 to 2.5 CV of 50 mM Ammonium acetate+8 M urea pH 4.0.

After elution, the column is cleaned with 1.5 to 2.5 CV of 50 mM Ammonium acetate+1M NaCl pH 4.0. This elution in 1M NaCl allows to eliminate DNA and endotoxins. Then, the column is sanitised with 1.5 to 2.5 CV 1M NaOH 1M+2M NaCl (2 h) and stored at room temperature in 20 mM NaOH.

3. Macroprep High S Cation Exchange Chromatography (MHS-E)—Positive Mode:

Cation exchange chromatography is conducted with Macroprep High S (Bio-Rad Laboratories cat. n° 156-0033) packed in a Vantage 180/500 column (Millipore BioProcess Division cat n° 87018001). The column is packed in highly purified water at an eluent flow rate of 260 cm/h (66.1 l/h). The dimensions of the packed column bed are: diameter 18 cm, cross-sectional area=254.4 cm$^2$, bed=36 cm, packed volume=9.16±0.25 l.

The column is sanitised with 1.5 to 2.5 CV of 1M NaOH+2M NaCl with a contact time of 2 hours at a flow rate of 40 l/h (157 cm/h). Maximum flow rate can be 250 cm/h. The pH is stabilised with 1.5 to 2.5 CV of 50 mM Ammonium acetate+2 M NaCl pH 2.0. The column is then equilibrated with 4 to 5.5 CV of 50 mM Ammonium acetate pH 2.0.

The pH of the QSFF-FT fraction (see section 2) is adjusted to 2.0 with 37% HCl. This solution is loaded without prior dilution at a flow rate of 125 cm/h (±31.8 l/h). The binding capacity of the gel is 5 to 15 mg/ml matrix. After loading, the column is equilibrated with 2 to 3 CV of 50 mM Ammonium acetate pH 2.0 at a flow rate of 157 cm/h (40 l/h). Maximum flow rate is 200 cm/h.

Elution is performed with a conductivity linear gradient on 10 CV between 25% (0.5M NaCl) and 75% (1.5M NaCl) with 50 mM Ammonium acetate pH 2.0 and 50 mM Ammonium acetate+2M NaCl pH 2.0. Elution is performed at a flow rate of 157 cm/h (40 l/h). Maximum flow rate is 200 cm/h. The eluted peak is collected in 2 liters fractions which are analysed by SDS-PAGE before pooling. After pooling, the MHS-E pool is stored at −20° C. until the next purification step or at 2-8° C. if used within 24 hours.

Then, the column is sanitised with 1.5 to 2.5 CV 1M NaOH 1M+2M NaCl (2 h) and stored at room temperature in 20 mM NaOH.

4. Concentration—Diafiltration

The concentration is conducted with two Sartocon cassette (0.6 m$^2$, cut-off 5 kDa) Hydrosart Sartorius membranes (Sartopore cat n° 302 144 2906 E-SG). The membranes are mounted in a holder connected to a Proflux M12 system (Millipore Bioprocess Division). The membrane is rinsed with water for injection (WFI). The sanitisation is performed by continuous recirculation of 0.5 M NaOH for 60 minutes. Then, the membrane is rinsed with Na$_2$HPO$_4$.12H$_2$O 20 mM pH 7.0, until permeate pH=7.0±0.1. Then, the membrane is equilibrated with PBS pH 7.4 (NaCl 8 g/l, KH$_2$PO$_4$ 0.19 g/l, Na$_2$HPO$_4$ 2.38 g/l) until permeate pH=7.4±0.1.

The inlet pressure and outlet pressures are set to 1.5±0.1 bar and 1.2±0.1 bar respectively.

The several Macroprep High S eluates are pooled together and, according to the total amount of protein, are concentrated to a volume corresponding to a theoretical concentration of 30 mg/ml. After concentration, the retentate is diafiltrated against 10 volumes of PBS pH 7.4 (NaCl 8 g/l, KH$_2$PO$_4$ 0.19 g/l, Na$_2$HPO$_4$ 2.38 g/l). The retentate is collected and 7 washes of the membrane are carried out, each one with 150 ml of PBS pH 7.4 (NaCl 8 g/l, KH$_2$PO$_4$ 0.19 g/l, Na$_2$HPO$_4$ 2.38 g/l) during 3 minutes with the same process parameters. The permeate line is closed during the washes.

A BCA protein assay is carried out on the retentate and each separate wash fractions. The retentate is pooled with selected wash fractions to obtain a total concentration superior to 12 mg/ml with a yield superior to 90%, if possible.

The membrane is rinsed with WFI. The sanitisation is performed by continuous recirculation of 0.5 M NaOH for 60 minutes. The membrane is then stored in NaOH 0.1 M.

5. Sterile Filtration

Sterile filtration of the retentate+the selected wash fractions is performed on a 1000 cm$^2$ 0.45/0.22 Sartopore 2 filter (Sartorius cat n° 544-1307-H8-00) at room temperature. The membrane is rinsed with about 500 ml of PBS pH 7.4 (NaCl 8 g/l, KH$_2$PO$_4$ 0.19 g/l, Na$_2$HPO$_4$ 2.38 g/l) before use.

The filtration is performed with a peristaltic pump at a flow rate of about 100 ml/min and the filtrate is collected in sterile and pyrogen free 5 L or 10 L single-use bottle.

According to a BCA assay performed on the filtrated bulk, the concentration is adjusted to 10 mg/ml with PBS pH 7.4 (NaCl 8 g/l, KH$_2$PO$_4$ 0.19 g/l, Na$_2$HPO$_4$ 2.38 g/l) added by filtration. After sampling, the sterile bulk is aliquoted in PETG 2000 ml Nalgene bottles (±1500 ml to 1700 ml/bottles). The sterile bulk is stored at −20° C. A schematic summary of production steps is provided in FIG. 1.

EXAMPLE 4 hH1.3 and Bis-Met hH1.3 Purification Efficiency

Culture of BL21[DE3]-bis-met rH1.3 in 50 L fermenter resulted in a yield at harvest time of at least 600 mg/L of culture, as assessed by SDS page analysis on serial dilution of total lysed cells. Final yield after the complete purification process was in excess of 500 mg/L of purified bis-met rH13.

Culture of BL21[DE3]-hH1.3 in 50 L fermenter resulted in a yield at harvest time of at least 600 mg/L of culture, as assessed by SDS page analysis on serial dilution of total lysed cells. The cells were processed through homogenisation and precipitation with HClO$_4$ according to the standard protocol. The results obtained were according to expectation. Loading on the MacroPrep High-S was also performed as usual, however, the rhH1.3 protein could not be eluted from the column using the conductivity linear gradient on 10 CV between 30% (0.6M NaCl) and 75% (1.5M NaCl) with 10 mM NaCH$_3$COO pH 2.0 and 10 mM NaCH$_3$COO+2 M NaCl pH 2.0. Although the rhH1.3 protein was eluted at 2 M NaCl, this step did not allow for sufficient purification and the protein could not be further processed. Thus, the purification has to be considered as failed. This failure was confirmed on two independent purification trials made from two different fermentations.

EXAMPLE 5

Effect of Bis-Met Histone H1.3 In Vitro

Inhibition Zone Assay

To measure the effect of recombinant histone as an antimicrobial and antiviral agent an inhibition zone assay was performed according to standard methods. Furthermore, the effect of recombinant histone as an antifungal agent was tested. Bacteria and fungi were grown in the presence of the bis-met histone H1.3 produced according to the methods outlined above and the average zone diameter was determined (see table 1).

Both gram-positive and gram-negative bacteria and fungi are efficiently eliminated as shown in table 1.

TABLE 1

Inhibition Zone Assay

| Target Organism | Drug Concentration [µg/µl] | Average Zone Diameter [mm] |
| --- | --- | --- |
| Bacillus megaterium | 5 | 11.4 |
| | 2.50 | 10.5 |
| | 1.25 | 9.7 |
| | 0.625 | 8.6 |
| | 0.31 | 7.9 |
| | Positive control LL-37 | 9.8 |
| Escherichia coli D21 | 20.00 | 7.4 |
| | 10.00 | 6.3 |
| | 5.00 | 4.8 |
| | 2.50 | 0 |
| | 1.25 | 0 |
| | Positive control LL-37 | 5 |
| Candida albicans | 20.00 | 11.8 |
| | 5.00 | 8.1 |
| | 2.50 | 6.1 |
| | 1.25 | 4.4 |
| | Positive control Nystain | 20.9 |

Cytotoxicity Assay:

This cell test is detecting the toxic effect of the histone on a histone-sensitive leukemia cell line (e.g. U-937). The vitality of leukemia cancer cells after incubation at different histone concentrations is monitored by means of the AlamarBlue assay, based on the observation of the fluorescence of the redox indicator, which is changing in response to the vitality of the cell. The histone anticancer activity is characterized by $IC_{50}$, which corresponds to the histone concentration by which the 50% cancer cell viability is observed. The batches used for the cytotoxicity assay as well as the clinical trials are summarised in table 2. As shown in Table 1, all tested samples show similar, high cytotoxicity against the tumor cell line U-937, irrespective of different contents of H1.3 and bis-Met (cf. Table 3).

TABLE 2

Cytotoxicity of Batches used in the Clinical Trial

| Sample (drug product) | $IC_{50}$ [µM] |
| --- | --- |
| Batch 1: M-H1A-P02 | 3.2 ± 0.5 |
| Batch 2: M-H1A-Pool01 | 3.1 ± 0.5 |
| Batch 3: M-H1A-Pool02 | 3.1 ± 0.5 |
| Batch 4: M-H1A-Pool03 | 2.2 ± 0.5 |

In addition to the bacteria and fungi shown in table 1, further bacteria, fungi and viruses may conveniently be tested by methods known in the art, such as any of the methods outlined herein. Non-limiting examples include Epstein-Barr-Virus, *Staphylococcus aureus*, *Aspergillus niger*, *Enterococcus*, *Pseudomonas*, *Haemophilus influenzae* and *Salmonella*.

EXAMPLE 6

Clinical Data

A phase I/II dose-escalation-trial to evaluate the maximum tolerable dose (MTD) of recombinant human histone H1.3 (rhH1.3) in patients with relapsed or refractory AML and in patients that refused chemotherapy or that are not eligible for chemotherapy was carried out. Inclusion criteria of patients were: signed informed consent, any race, both gender, at least 18 years of age, cytologically proven AML with at least 20% blasts in bone marrow, failure after, unfit for or refusal of standard chemotherapy, adequate performance state (Karnowsky index>60%) and a life expectancy of at least 30 days. Criteria that lead to exclusion of patients were significant organ deficiency, known HIV infection, known hepatitis C virus or hepatitis B virus infection, gravidity or nursing, other malignancies, circulating anti-H1 antibodies, heparin treatment during the two weeks before Visit 1 or during study participation, active medical conditions known to potentially interfere with rhH1.3 treatment such as rheumatoid arthritis or systemic lupus erythematodes (SLE) as well as alcohol and/or drug abuse.

Design of the Study

Patients received 3 infusions per week in three consecutive weeks. The initial dose was 38 mg/m². The dose escalation scheme used is shown in table 3.

TABLE 3

Dose Escalation Scheme

| Dose Level | Dose in mg/m² | Number of Patients Planned | Tested | Treatment |
| --- | --- | --- | --- | --- |
| 1 | 38 | 3 | 7 | Complete |
| 2 | 60 | 3 | 7 | Complete |
| 3 | 96 | 3 | 3 | Complete |
| 4 | 153 | 3 | 3 | Complete |
| New Dose Escalation | | | | |
| 5, 5, 6 | 245, 245, 392 | 1 (cycle 1) | 1 | Complete |
| 6, 6, 7 | 392, 392, 628 | (cycle 2, the same patient as above) | | Complete |
| 6, 6, 7 | 392, 392, 628 | 1 | 1 | Complete |

The clinical trial Phase I/II was done in the Saarland University Hospital in Homburg with AML (acute myeloic leukemia) patients. The drug product batches used in this trial were: B1, B2, B3 and B4. The characteristics of these four batches and of one GLP batch, used in the toxicology study are presented in the table 4 below:

TABLE 4

Characteristics of Batches of Polypeptide used in the Study

| Batches | Description | Endotoxin [EU/mg] | Evaluation-Endotoxin Level | Rh H1.3 MS peaks [Da] | Anticancer activity in cell Test $IC_{50}$ [µM] |
| --- | --- | --- | --- | --- | --- |
| L-H1A-03B07* | | 5 | below AL | H1.3 + bis Met | 1.7-2.7 |
| M-H1A-P02 | B1 | 12 | above AL | H1.3 + bis Met | 3.2 |
| M-H1A-Pool01 | B2 | 95 | above AL | mainly bis Met | 3.1 |

TABLE 4-continued

| | | | | | |
|---|---|---|---|---|---|
| M-H1A-Pool02 | B3 | 0.8 | below AL | mainly bis Met | 3.1 |
| M-H1A-Pool03 | B4 | 1.7 | below AL | mainly bis Met | 2.2 |

\* Used in tox study, not clinical study
AL: acceptable limit
MS peak:  22221 Da  H1.3  no Met
          22481 Da  bis Met  N-terminal Met-Met

6.1 Preliminary Evaluation

The table 5 summarizes the preliminary clinical results of the first 22 AML patients treated with recombinant human histone H1.3 (rh H1.3, "Oncohist") at increasing dose levels (the so-called Fibonacci scheme).

Patients WW13 and WW27 received two treatment cycles each (one cycle comprised 3 infusions a week over three weeks, altogether 9). WW27 had a dose escalation in each cycle i.e. 5-5-6: two weeks dose level 5, third week dose level 6 and similarly in the second cycle dose levels: 6-6-7.

TABLE 5

Clinical Results of AML Patients Treated with Recombinant Human Histone H1.3 ("Oncohist") Obtained in the Preliminary Evaluation

| Patient Initials & No. | Dose Level | Remarks | Drug Product Batch | Composition According to MS (H1.3, bis Met)* | Endotoxin Contamination [EU/mg] | Side Effects |
|---|---|---|---|---|---|---|
| AS 01 | 1 | TTI | B1 | H1.3 + bis Met | 12 | moderately tolerated |
| NM 02 | 1 | TTI | B1 | H1.3 + bis Met | | badly tolerated |
| HS 03 | 1 | TLI | B1 | H1.3 + bis Met | | well tolerated |
| RH 04 | 1 | TTI | B1 | H1.3 + bis Met | | well tolerated |
| MF 05 | 1 | TTI, TLI | B1 | H1.3 + bis Met | | badly tolerated |
| RS 07 | 1 | TTI | B1 | H1.3 + bis Met | | well tolerated |
| PS 10 | 1 | TTI | B1-21 vials B2-4 vials | H1.3 + bis Met | | well tolerated |
| MT 11 | 2 | | B2 | Mainly bis Met | 95 | badly tolerated |
| MG 12 | 2 | TLI | B2 | Mainly bis Met | | badly tolerated |
| WW 13 | 2 | PR, TN | B2 | Mainly bis Met | | badly tolerated |
| AH 15 | 2 | TTI, TLI | B2 | Mainly bis Met | | badly tolerated |
| GB 16 | 2 | TN, TLI | B2 | Mainly bis Met | | badly tolerated |
| HF 18 | 2 | TTI, TLI | B2 | Mainly bis Met | | badly tolerated |
| Start of Histone Drug without Endotoxin | | | | | | |
| ES 19 | 2 | PR, TTI, TLI | B3 | Mainly bis Met | 0.8 | NSE |
| IG 20 | 3 | | B3 | Mainly bis Met | | NSE |
| BG 21 | 3 | TTI | B3 | Mainly bis Met | | NSE |
| GR 22 | 3 | | B3 | Mainly bis Met | | NSE |
| EL 23 | 4 | TTI, TLI | B3 | Mainly bis Met | | NSE |
| EW 24 | 4 | | B3 | Mainly bis Met | | NSE |
| BH 26 | 4 | | B3 | Mainly bis Met | | NSE |
| WW 27 | C1: 5, 5, 6 C2: 6, 6, 7 | PR, TTI | B3/B4 | Mainly bis Met | B4: 1.7 | NSE |
| PF 28 | 6, 6, 7 | | B3 | Mainly bis Met | | NSE |

*preliminary analysis
PR: partial remission
TTI: temporary thrombocyte increase
TN: thrombocytes with normal levels
TLI: temporary leukocyte increase
NSE: no side effects
H1.3: mature recombinant human histone H1.3; bis Met: N-Met-Met-H1.3

As is evident from Table 5, drug side effects occur only as a consequence of endotoxin contamination (see also Table 3). Both the naturally occurring histone H1.3 and the "bis Met" derivative show similar properties as far as clinical signs of efficacy are concerned.

Immunogenicity

All patients were screened for the existence of anti-histone H1.3 autoantibodies before, during and after treatment. None of the treated patients developed autoantibodies during the treatment, neither those with one treatment cycle nor those who received two cycles. Histone H1 is an evolutionary very conservative protein and is neither expected nor proven to be immunogenic. The clinical data confirm that no immunogenic activity can be observed using either the naturally occurring histone H1.3 or the "bis Met" derivative.

Therapeutic Effects

About 50% of the patients showed an increase of thrombocytes and part of them also increase of leukocytes, both very critical biomarkers for AML. Three patients had a partial remission (decrease of tumor cells to less than 50% the initial value. Patient WW13 showed an increase of thrombocytes to normal level ($210 \times 10^9/l$) which lasted 18 months. His thrombocyte count before the treatment with Oncohist was equal to $47 \times 10^9/l$.

6.2 Final Evaluation of Clinical Results

Table 6 summarizes the clinical results obtained after more detailed analysis of the 22 AML patients treated with recombinant human histone H1.3 (rh H1.3, "Oncohist") at increasing dose levels (Fibonacci scheme).

As described above, patients WW13 and WW27 had received two treatment cycles each (one cycle comprised 3 infusions a week over three weeks, altogether 9). WW27 had a dose escalation in each cycle i.e. 5-5-6: two weeks dose level 5, third week dose level 6 and similarly in the second cycle dose levels: 6-6-7.

to cytostatics. This result is in accordance with preclinical studies, showing that the recombinant human histone H1.3 derivative does not damage healthy blood cells and does not cause resistance.

TABLE 6

Clinical Results of AML Patients Treated with Recombinant Human Histone H1.3 ("Oncohist") Obtained in the Final Evaluation

| Patient Initials & No. | Dose Level | Remarks | Drug Product Batch | Composition According to MS (H1.3, bis Met)* | Endotoxin Contamination [EU/mg] | Side Effects |
|---|---|---|---|---|---|---|
| AS 01 | 1 | | B1 | H1.3 + bis Met | 12 | moderately tolerated |
| NM 02 | 1 | TI, LI | B1 | H1.3 + bis Met | | poorly tolerated |
| HS 03 | 1 | TLI | B1 | H1.3 + bis Met | | moderately tolerated |
| RH 04 | 1 | | B1 | H1.3 + bis Met | | well tolerated |
| MF 05 | 1 | | B1 | H1.3 + bis Met | | poorly tolerated |
| RS 07 | 1 | | B1 | H1.3 + bis Met | | well tolerated |
| PS 10 | 1 | | B1-21 vials B2-4 vials | H1.3 + bis Met | | well tolerated |
| MT 11 | 2 | | B2 | Mainly bis Met | 95 | poorly tolerated |
| MG 12 | 2 | LI | B2 | Mainly bis Met | | poorly tolerated |
| WW 13 | 2 | PR, TN | B2 | Mainly bis Met | | poorly tolerated |
| AH 15 | 2 | LI | B2 | Mainly bis Met | | poorly tolerated |
| GB 16 | 2 | | B2 | Mainly bis Met | | poorly tolerated |
| HF 18 | 2 | | B2 | Mainly bis Met | | poorly tolerated |
| Start of Histone Drug without Endotoxin | | | | | | |
| ES 19 | 2 | PR, TI | B3 | Mainly bis Met | 0.8 | well tolerated |
| IG 20 | 3 | | B3 | Mainly bis Met | | well tolerated |
| BG 21 | 3 | TI | B3 | Mainly bis Met | | well tolerated |
| GR 22 | 3 | | B3 | Mainly bis Met | | well tolerated |
| EL 23 | 4 | TI[b], LI | B3 | Mainly bis Met | | well tolerated |
| EW 24 | 4 | | B3 | Mainly bis Met | | well tolerated |
| BH 26 | 4 | | B3 | Mainly bis Met | | well tolerated |
| WW 27 | C1: 5, 5, 6 C2: 6, 6, 7 | PR, TI, LI | B3/B4 | Mainly bis Met | B4: 1.7 | well tolerated |
| PF 28 | 6, 6, 7 | | B3 | Mainly bis Met | | Day 8**, day 19 SAE*** |

*preliminary analysis
**after one of 9 infusions AE, recovered
***during last infusion SAE, atrial fibrillation in 74 years patient, relation questionable
PR: partial remission
TI: thrombocyte increase
TN: thrombocytes with normal levels
LI: leukocyte increase
AE: adverse events; SAE: serious adverse events
H1.3: mature recombinant human histone H1.3; bis Met: N-Met-Met-H1.3

Therapeutic Effects

According to the final evaluation, seven of 22 patients showed an increase of thrombocytes and part of them also increase of leukocytes, both very critical biomarkers for AML. Three patients had a partial remission (decrease of tumor cells to less than 6-25% with concomitant improvement of other blood values). Patient WW13 showed an increase of thrombocytes to normal level ($210 \times 10^9$/l) which lasted 18 months. His thrombocyte count before the treatment with Oncohist was equal to $47 \times 10^9$/l.

Safety Evaluation

A Clinical Study Report showed that rhH1.3 (Oncohist) is safe at doses treated so far. No serious side-effects were observed except for one atrial fibrillation under infusion of rhH1.3, which was considered to be possibly related to the study drug. Seventeen (17) patients completed one course of therapy (8-9 administrations), and two responding patients received a second course without side effects. No dose-limiting toxicities were observed and the maximal tolerated dose has not been reached at 628 mg/m$^2$.

Most importantly, the pure, endotoxin-free study drug was tolerated well by patients, i.e. without side effects, contrary

EXAMPLE 7

Evaluation of the Presence of Bis-Met hH1.3 in a Sample

The "bis-Met" histone hH1.3 is easily distinguished by MS from endogenous histone H1. This can be analysed directly with ESI-QTOF detection of original unprocessed rhH1.3 drug product solution or in an RP-HPLC-ESI-MS process with RP-HPLC chromatographic separation and subsequent ESI-MS detection. As can be seen in FIG. 2, batch B1 contains both histone H1.3 and the N-Met-Met-derivative. FIG. 3 shows one of three batches (B2) which consist mainly of N-Met-Met-H1.3. Independent of composition, the different batches show comparable cytotoxic activity against leukemia cells (Table 3).

The following spectra were obtained by tandem mass spectrometry (QTOF, a combination of quadrupole and time-of-flight spectrometry in a single instrument). As can be seen in FIG. 2, batch B1 contains both histone H1.3 and the N-Met-Met-derivative. FIG. 3 shows one of three batches (B2) which consist mainly of N-Met-Met-H1.3. Independent of composition, the different batches show comparable cytotoxic activity against leukemia cells (Table 3).

The invention claimed is:

1. A bis-met histone polypeptide comprising two methionine residues as first and second N-terminal amino acid residues linked via a peptide bond to a mature eukaryotic H1 histone.

2. The bis-met histone polypeptide of claim 1, wherein the mature eukaryotic H1 histone is a histone H1.0, a histone H1.1, a histone H1.2, a histone H1.3, a histone H1.4, a histone H1.5 or a histone H1t.

3. The bis-met histone polypeptide of claim 1, wherein an amino acid sequence including the second N-terminal amino acid residue, the peptide bond and the mature eukaryotic H1 histone is SEQ ID NO: 7, SEQ ID NO: 9, SEQ ID NO: 11 or SEQ ID NO: 13.

4. The bis-met histone polypeptide of claim 1, wherein an amino acid sequence including the second N-terminal amino acid residue, the peptide bond and the mature eukaryotic H1 histone is one having at least 85% sequence identity to SEQ ID NO: 7, SEQ ID NO: 9, SEQ ID NO: 11 or SEQ ID NO: 13 and retaining at least 20% of its biological activity.

5. The bis-met histone polypeptide of claim 4, wherein the amino acid sequence retains at least 50% of its biological activity.

6. The bis-met histone polypeptide of claim 5, wherein the amino acid sequence retains at least 75% of its biological activity.

7. The bis-met histone polypeptide of claim 6, wherein the amino acid sequence retains at least 80% of its biological activity.

8. The bis-met histone polypeptide of claim 7, wherein the amino acid sequence retains at least 85% of its biological activity.

9. The bis-met histone polypeptide of claim 8, wherein the amino acid sequence retains at least 90% of its biological activity.

10. The bis-met histone polypeptide of claim 9, wherein the amino acid sequence retains at least 95% of its biological activity.

11. The bis-met histone polypeptide of claim 4, wherein the amino acid sequence is one having at least 90% sequence identity to SEQ ID NO: 7, SEQ ID NO: 9, SEQ ID NO: 11 or SEQ ID NO: 13.

12. The bis-met histone polypeptide of claim 11, wherein the amino acid sequence is one having at least 95% sequence identity to SEQ ID NO: 7, SEQ ID NO: 9, SEQ ID NO: 11 or SEQ ID NO: 13.

13. The bis-met histone polypeptide of claim 1 which is SEQ ID NO: 3.

14. A composition comprising the bis-met histone polypeptide of claim 1 and optionally comprising a pharmaceutically acceptable carrier and/or a diluent.

15. The composition of claim 14 further comprising a mature eukaryotic histone.

16. The composition of claim 15, wherein the mature eukaryotic histone is a histone H1 or a histone H2A.

17. The composition of claim 14, wherein the bis-met histone polypeptide comprises the amino acid sequence of SEQ ID NO: 3.

18. The composition of claim 17, wherein the bis-met histone polypeptide consists essentially of the amino acid sequence of SEQ ID NO: 3.

19. The composition of claim 18, wherein the bis-met histone polypeptide has the amino acid sequence of SEQ ID NO: 3.

20. A method of treating a leukemia, the method comprising administering a composition of claim 14 to an individual in need thereof, wherein the disease is a leukemia.

21. The method of claim 20, wherein the leukemia is acute myeloic leukemia.

* * * * *

SEQUENCE LISTING

<160> NUMBER OF SEQ ID NOS: 14

<210> SEQ ID NO 1
<211> LENGTH: 220
<212> TYPE: PRT
<213> ORGANISM: Homo Sapiens

<400> SEQUENCE: 1

Ser Glu Thr Ala Pro Leu Ala Pro Thr Ile Pro Ala Pro Ala Glu Lys
1               5                   10                  15

Thr Pro Val Lys Lys Lys Ala Lys Lys Ala Gly Ala Thr Ala Gly Lys
            20                  25                  30

Arg Lys Ala Ser Gly Pro Pro Val Ser Glu Leu Ile Thr Lys Ala Val
        35                  40                  45

Ala Ala Ser Lys Glu Arg Ser Gly Val Ser Leu Ala Ala Leu Lys Lys
    50                  55                  60

Ala Leu Ala Ala Ala Gly Tyr Asp Val Glu Lys Asn Asn Ser Arg Ile
65                  70                  75                  80

Lys Leu Gly Leu Lys Ser Leu Val Ser Lys Gly Thr Leu Val Gln Thr
                85                  90                  95

Lys Gly Thr Gly Ala Ser Gly Ser Phe Lys Leu Asn Lys Lys Ala Ala
            100                 105                 110

Ser Gly Glu Gly Lys Pro Lys Ala Lys Lys Ala Gly Ala Ala Lys Pro
        115                 120                 125

Arg Lys Pro Ala Gly Ala Ala Lys Lys Pro Lys Lys Val Ala Gly Ala
    130                 135                 140

Ala Thr Pro Lys Lys Ser Ile Lys Lys Thr Pro Lys Lys Val Lys Lys
145                 150                 155                 160

Pro Ala Thr Ala Ala Gly Thr Lys Lys Val Ala Lys Ser Ala Lys Lys
                165                 170                 175

Val Lys Thr Pro Gln Pro Lys Lys Ala Ala Lys Ser Pro Ala Lys Ala
            180                 185                 190

Lys Ala Pro Lys Pro Lys Ala Ala Lys Pro Lys Ser Gly Lys Pro Lys
        195                 200                 205

Val Thr Lys Ala Lys Lys Ala Ala Pro Lys Lys Lys
    210                 215                 220

<210> SEQ ID NO 2
<211> LENGTH: 678
<212> TYPE: DNA
<213> ORGANISM: Artificial Sequence
<220> FEATURE:
<223> OTHER INFORMATION: Nucleic acid sequence encoding open reading
      frame of bis-met histone rH1.3

<400> SEQUENCE: 2
tcatgatgtc cgaaaccgct ccgctggctc cgaccatccc ggctccggct gaaaaaccc      60 cggttaagaa aaaggctaaa aaagctggtg ctaccgctgg taaacgtaaa gcttccggtc    120
cgccggtttc cgaactgatc accaaagctg ttgctgcttc caagaacgt tccggtgttt     180 ccctggctgc tctgaaaaaa gctctggctg ctgctggtta cgacgttgag aaaaacaact    240
cccgtatcaa actgggtctg aaatccctgg tttccaaagg caccctggtt cagaccaaag    300
gcaccggtgc ttccggttcc ttcaaactga acaaaaaagc tgcttccggt gaaggtaaac    360
cgaaagctaa gaaagcgggt gcggctaaac cgcgtaaacc ggctggtgct gctaaaaaac    420
cgaaaaaagt tgctggtgct gctaccccga aaaaatccat caagaaaacc ccgaaaaaag    480

```
ttaaaaaacc ggctaccgct gctggcacca aaaaagttgc taaatccgct aaaaaagtta        540
aaaccccgca gccgaaaaaa gctgctaaat ccccggctaa agctaaagct ccgaaaccga        600
aagctgctaa accgaaatcc ggtaaaccga agttaccaa agctaaaaag gctgctccga         660
aaaagaaata atggatcc                                                      678
```

<210> SEQ ID NO 3
<211> LENGTH: 222
<212> TYPE: PRT
<213> ORGANISM: Artificial Sequence
<220> FEATURE:
<223> OTHER INFORMATION: recombinant polypeptide bis-met histone rH1.3

<400> SEQUENCE: 3

```
Met Met Ser Glu Thr Ala Pro Leu Ala Pro Thr Ile Pro Ala Pro Ala
1               5                   10                  15

Glu Lys Thr Pro Val Lys Lys Lys Ala Lys Ala Gly Ala Thr Ala
            20                  25                  30

Gly Lys Arg Lys Ala Ser Gly Pro Pro Val Ser Glu Leu Ile Thr Lys
        35                  40                  45

Ala Val Ala Ala Ser Lys Glu Arg Ser Gly Val Ser Leu Ala Ala Leu
    50                  55                  60

Lys Lys Ala Leu Ala Ala Ala Gly Tyr Asp Val Glu Lys Asn Asn Ser
65                  70                  75                  80

Arg Ile Lys Leu Gly Leu Lys Ser Leu Val Ser Lys Gly Thr Leu Val
                85                  90                  95

Gln Thr Lys Gly Thr Gly Ala Ser Gly Ser Phe Lys Leu Asn Lys Lys
            100                 105                 110

Ala Ala Ser Gly Glu Gly Lys Pro Lys Ala Lys Lys Ala Gly Ala Ala
        115                 120                 125

Lys Pro Arg Lys Pro Ala Gly Ala Ala Lys Lys Pro Lys Lys Val Ala
    130                 135                 140

Gly Ala Ala Thr Pro Lys Lys Ser Ile Lys Lys Thr Pro Lys Lys Val
145                 150                 155                 160

Lys Lys Pro Ala Thr Ala Ala Gly Thr Lys Lys Val Ala Lys Ser Ala
                165                 170                 175

Lys Lys Val Lys Thr Pro Gln Pro Lys Lys Ala Ala Lys Ser Pro Ala
            180                 185                 190

Lys Ala Lys Ala Pro Lys Pro Lys Ala Ala Lys Pro Lys Ser Gly Lys
        195                 200                 205

Pro Lys Val Thr Lys Ala Lys Lys Ala Ala Pro Lys Lys Lys
    210                 215                 220
```

<210> SEQ ID NO 4
<211> LENGTH: 675
<212> TYPE: DNA
<213> ORGANISM: Artificial Sequence
<220> FEATURE:
<223> OTHER INFORMATION: Nucleic acid encoding orpen reading frame for
      histone rH1.3

<400> SEQUENCE: 4

```
tcatgagcga aaccgcgccg ctggcgccga ccattccggc gccggcggaa aaaccccgg         60 ttaaaaaaaa agcgaaaaaa gccggtgcga ccgcgggtaa acgtaaagcg agcggtccgc        120
cggttagcga actgattacc aaagcggttg cggcagcaa agaacgtagc ggtgttagcc         180
tggcggcgct gaaaaaagcg ctggcggcgg cgggttatga tgtggaaaaa aacaacagcc       240
```

```
gcatcaaact gggtctgaaa agcctggtta gcaaaggcac cctggttcag accaaaggca      300
ccggtgcgag cggtagcttt aaactgaaca aaaaagcggc gagcggtgaa ggtaaaccga      360
aagccaaaaa agcgggcgcg gcgaaaccgc gtaaaccggc gggtgcggcg aaaaaaccga      420
aaaaagttgc gggtgcggcc accccgaaaa aaagcatcaa aaaaaccccg aaaaaagtga      480
aaaaaccggc caccgcggcg ggcaccaaaa aagtggcgaa agcgcgaaa aaagttaaaa      540 ccccgcagcc gaaaaaagcg gccaaaagcc cggcgaaagc gaaagcgccg aaaccgaaag      600
cggccaaacc gaaaagcggt aaaccgaaag ttaccaaagc gaaaaaagcg gcgccgaaaa      660
aaaaataatg gatcc                                                      675
```

<210> SEQ ID NO 5
<211> LENGTH: 221
<212> TYPE: PRT
<213> ORGANISM: Artificial Sequence
<220> FEATURE:
<223> OTHER INFORMATION: recombinant polypeptide histone rH1.3

<400> SEQUENCE: 5

```
Met Ser Glu Thr Ala Pro Leu Ala Pro Thr Ile Pro Ala Pro Ala Glu
1               5                   10                  15

Lys Thr Pro Val Lys Lys Lys Ala Lys Ala Gly Ala Thr Ala Gly
            20                  25                  30

Lys Arg Lys Ala Ser Gly Pro Pro Val Ser Glu Leu Ile Thr Lys Ala
        35                  40                  45

Val Ala Ala Ser Lys Glu Arg Ser Gly Val Ser Leu Ala Ala Leu Lys
    50                  55                  60

Lys Ala Leu Ala Ala Ala Gly Tyr Asp Val Glu Lys Asn Asn Ser Arg
65                  70                  75                  80

Ile Lys Leu Gly Leu Lys Ser Leu Val Ser Lys Gly Thr Leu Val Gln
                85                  90                  95

Thr Lys Gly Thr Gly Ala Ser Gly Ser Phe Lys Leu Asn Lys Lys Ala
            100                 105                 110

Ala Ser Gly Glu Gly Lys Pro Lys Ala Lys Lys Ala Gly Ala Ala Lys
        115                 120                 125

Pro Arg Lys Pro Ala Gly Ala Ala Lys Lys Pro Lys Lys Val Ala Gly
    130                 135                 140

Ala Ala Thr Pro Lys Lys Ser Ile Lys Lys Thr Pro Lys Lys Val Lys
145                 150                 155                 160

Lys Pro Ala Thr Ala Ala Gly Thr Lys Lys Val Ala Lys Ser Ala Lys
                165                 170                 175

Lys Val Lys Thr Pro Gln Pro Lys Lys Ala Ala Lys Ser Pro Ala Lys
            180                 185                 190

Ala Lys Ala Pro Lys Pro Lys Ala Ala Lys Pro Lys Ser Gly Lys Pro
        195                 200                 205

Lys Val Thr Lys Ala Lys Lys Ala Ala Pro Lys Lys Lys
    210                 215                 220
```

<210> SEQ ID NO 6
<211> LENGTH: 642
<212> TYPE: DNA
<213> ORGANISM: Homo sapiens

<400> SEQUENCE: 6

```
atgtccgaga ctgctcctgc cgctcccgct gccgcgcctc ctgcggagaa ggcccctgta      60
aagaagaagg cggccaaaaa ggctgggggt acgcctcgta aggcgtccgg tccccccggtg    120
```
tcagagctca tcaccaaggc tgtggccgcc tctaaagagc gtagcggagt ttctctggct        180
gctctgaaaa aagcgttggc tgccgccggc tatgatgtgg agaaaaacaa cagccgtatc        240
aaacttggtc tcaagagcct ggtgagcaag ggcactctgg tgcaaacgaa aggcaccggt        300
gcttctggct cctttaaact caacaagaag gcagcctccg gggaagccaa gcccaaggtt        360
aaaaaggcgg gcggaaccaa acctaagaag ccagttgggg cagccaagaa gcccaagaag        420
gcggctggcg cgcaactcc gaagaagagc gctaagaaaa caccgaagaa agcgaagaag         480
ccggccgcgg ccactgtaac caagaaagtg gctaagagcc caagaaggc caaggttgcg         540 aagcccaaga agctgccaa aagtgctgct aaggctgtga agcccaaggc cgctaagccc         600
aaggttgtca agcctaagaa ggcggcgccc aagaagaaat ag                          642

<210> SEQ ID NO 7
<211> LENGTH: 213
<212> TYPE: PRT
<213> ORGANISM: Homo sapiens

<400> SEQUENCE: 7

Met Ser Glu Thr Ala Pro Ala Ala Pro Ala Ala Pro Ala Pro Ala Glu
1               5                   10                  15

Lys Ala Pro Val Lys Lys Ala Ala Lys Ala Gly Gly Thr Pro
                20                  25                  30         Arg Lys Ala Ser Gly Pro Pro Val Ser Glu Leu Ile Thr Lys Ala Val
                35                  40                  45

Ala Ala Ser Lys Glu Arg Ser Gly Val Ser Leu Ala Ala Leu Lys Lys
        50                  55                  60

Ala Leu Ala Ala Ala Gly Tyr Asp Val Glu Lys Asn Asn Ser Arg Ile
65                  70                  75                  80

Lys Leu Gly Leu Lys Ser Leu Val Ser Lys Gly Thr Leu Val Gln Thr
                85                  90                  95

Lys Gly Thr Gly Ala Ser Gly Ser Phe Lys Leu Asn Lys Lys Ala Ala
                100                 105                 110

Ser Gly Glu Ala Lys Pro Lys Val Lys Lys Ala Gly Gly Thr Lys Pro
                115                 120                 125

Lys Lys Pro Val Gly Ala Ala Lys Lys Pro Lys Ala Ala Gly Gly
            130                 135                 140

Ala Thr Pro Lys Lys Ser Ala Lys Lys Thr Pro Lys Lys Ala Lys Lys
145                 150                 155                 160

Pro Ala Ala Ala Thr Val Thr Lys Lys Val Ala Lys Ser Pro Lys Lys
                165                 170                 175

Ala Lys Val Ala Lys Pro Lys Lys Ala Ala Lys Ser Ala Ala Lys Ala
                180                 185                 190

Val Lys Pro Lys Ala Ala Lys Pro Lys Val Val Lys Pro Lys Lys Ala
                195                 200                 205

Ala Pro Lys Lys Lys
            210

<210> SEQ ID NO 8
<211> LENGTH: 666
<212> TYPE: DNA
<213> ORGANISM: Homo sapiens

<400> SEQUENCE: 8
atgtcggaga ctgctccact tgctcctacc attcctgcac ccgcagaaaa aacacctgtg        60

| | | |
|---|---|---|
| aagaaaaagg cgaagaaggc aggcgcaact gctgggaaac gcaaagcatc cggaccccca | 120 |
| gtatctgagc ttatcaccaa ggcagtggca gcttctaagg agcgcagcgg cgtttctctg | 180 |
| gccgcgctta agaaagcgct tgcggctgct ggctacgatg tagaaaaaaa caacagccgt | 240 |
| atcaagcttg gcctcaagag cttggtgagc aaaggtactc tggtgcagac caaaggtacc | 300 |
| ggtgcttctg gctccttcaa actcaacaag aaagcggctt ccggggaagg caaacccaag | 360 |
| gccaaaaagg ctggcgcagc caagcctagg aagcctgctg gggcagccaa gaagcccaag | 420 |
| aaggtggctg cgccgctac cccgaagaaa agcatcaaaa agactcctaa gaaggtaaag | 480 |
| aagccagcaa ccgctgctgg gaccaagaaa gtggccaaga gtgcgaaaaa ggtgaaaaca | 540 |
| cctcagccaa aaaagctgc caagagtcca gctaaggcca agcccctaa gcccaaggcg | 600 |
| gccaagccta gtcggggaa gccgaaggtt acaaaggcaa agaaggcagc tccgaagaaa | 660 |
| aagtga | 666 |

<210> SEQ ID NO 9
<211> LENGTH: 220
<212> TYPE: PRT
<213> ORGANISM: Homo sapiens

<400> SEQUENCE: 9

Met Ser Glu Thr Ala Pro Leu Ala Pro Thr Ile Pro Ala Pro Ala Glu
1               5                   10                  15

Lys Thr Pro Val Lys Lys Lys Ala Lys Ala Gly Ala Thr Ala Gly
            20                  25                  30

Lys Arg Lys Ala Ser Gly Pro Pro Val Ser Glu Leu Ile Thr Lys Ala
        35                  40                  45

Val Ala Ala Ser Lys Glu Arg Ser Gly Val Ser Leu Ala Ala Leu Lys
    50                  55                  60

Lys Ala Leu Ala Ala Ala Gly Tyr Asp Val Glu Lys Asn Asn Ser Arg
65                  70                  75                  80

Ile Lys Leu Gly Leu Lys Ser Leu Val Ser Lys Gly Thr Leu Val Gln
                85                  90                  95

Thr Lys Gly Thr Gly Ala Ser Gly Ser Phe Lys Leu Asn Lys Lys Ala
            100                 105                 110

Ala Ser Gly Glu Gly Lys Pro Lys Ala Lys Lys Ala Gly Ala Ala Lys
        115                 120                 125

Pro Arg Lys Pro Ala Gly Ala Ala Lys Lys Pro Lys Lys Val Ala Gly
    130                 135                 140

Ala Ala Thr Pro Lys Lys Ser Ile Lys Lys Thr Pro Lys Lys Val Lys
145                 150                 155                 160

Lys Pro Ala Thr Ala Ala Gly Thr Lys Lys Val Ala Lys Ser Ala Lys
                165                 170                 175

Lys Val Lys Thr Pro Gln Pro Lys Lys Ala Ala Lys Ser Pro Ala Lys
            180                 185                 190

Ala Lys Ala Pro Lys Pro Lys Ala Ala Lys Pro Lys Ser Gly Lys Pro
        195                 200                 205

Lys Val Thr Lys Ala Lys Lys Ala Ala Pro Lys Lys
    210                 215                 220

<210> SEQ ID NO 10
<211> LENGTH: 660
<212> TYPE: DNA
<213> ORGANISM: Homo sapiens

<400> SEQUENCE: 10

-continued

```
atgtccgaga ctgcgcctgc cgcgcccgct gctccggccc ctgccgagaa gactcccgtg    60
aagaagaagg cccgcaagtc tgcaggtgcg gccaagcgca aagcgtctgg gcccccggtg   120
tccgagctca ttactaaagc tgttgccgcc tccaaggagc gcagcggcgt atctttggcc   180
gctctcaaga aagcgctggc agccgctggc tatgacgtgg agaaaaacaa cagccgcatc   240
aagctgggtc tcaagagcct ggtgagcaag ggcaccctgg tgcagaccaa gggcaccggc   300
gcgtcgggtt ccttcaaact caacaagaag gcggcctctg ggaagccaa gcctaaggct   360 aaaaaggcag gcgcggccaa ggccaagaag ccagcaggag cggcgaagaa gcccaagaag   420
gcgacggggg cggccacccc caagaagagc gccaagaaga ccccaaagaa ggcgaagaag   480
ccggctgcag ctgctggagc caaaaaagcg aaaagcccga aaaggcgaa agcagccaag   540 ccaaaaaagg cgcccaagag cccagcgaag gccaagcag ttaaacccaa ggcggctaaa   600
ccaaagaccg ccaagcccaa ggcagccaag ccaaagaagg cggcagccaa gaaaaagtag   660
```

<210> SEQ ID NO 11
<211> LENGTH: 219
<212> TYPE: PRT
<213> ORGANISM: Homo sapiens

<400> SEQUENCE: 11

```
Met Ser Glu Thr Ala Pro Ala Ala Pro Ala Ala Pro Ala Pro Ala Glu
1               5                   10                  15

Lys Thr Pro Val Lys Lys Lys Ala Arg Lys Ser Ala Gly Ala Ala Lys
            20                  25                  30

Arg Lys Ala Ser Gly Pro Pro Val Ser Glu Leu Ile Thr Lys Ala Val
        35                  40                  45

Ala Ala Ser Lys Glu Arg Ser Gly Val Ser Leu Ala Ala Leu Lys Lys
    50                  55                  60

Ala Leu Ala Ala Ala Gly Tyr Asp Val Glu Lys Asn Asn Ser Arg Ile
65                  70                  75                  80

Lys Leu Gly Leu Lys Ser Leu Val Ser Lys Gly Thr Leu Val Gln Thr
                85                  90                  95

Lys Gly Thr Gly Ala Ser Gly Ser Phe Lys Leu Asn Lys Lys Ala Ala
            100                 105                 110

Ser Gly Glu Ala Lys Pro Lys Ala Lys Lys Ala Gly Ala Ala Lys Ala
        115                 120                 125

Lys Lys Pro Ala Gly Ala Ala Lys Lys Pro Lys Ala Thr Gly Ala
    130                 135                 140

Ala Thr Pro Lys Lys Ser Ala Lys Lys Thr Pro Lys Lys Ala Lys Lys
145                 150                 155                 160

Pro Ala Ala Ala Gly Ala Lys Lys Ala Lys Ser Pro Lys Lys Ala
                165                 170                 175

Lys Ala Ala Lys Pro Lys Lys Ala Pro Lys Ser Pro Ala Lys Ala Lys
            180                 185                 190

Ala Val Lys Pro Lys Ala Ala Lys Pro Lys Thr Ala Lys Pro Lys Ala
        195                 200                 205

Ala Lys Pro Lys Lys Ala Ala Ala Lys Lys Lys
    210                 215
```

<210> SEQ ID NO 12
<211> LENGTH: 681
<212> TYPE: DNA
<213> ORGANISM: Homo sapiens

<400> SEQUENCE: 12

```
atgtcggaaa ccgctcctgc cgagacagcc accccagcgc cggtggagaa atccccggct      60
aagaagaagg caactaagaa ggctgccggc gccggcgctg ctaagcgcaa agcgacgggg     120
ccccagtct cagagctgat caccaaggct gtggctgctt ctaaggagcg caatggcctt     180
tctttggcag cccttaagaa ggccttagcg gccggtggct acgacgtgga agaataac      240
agccgcatta agctgggcct caagagcttg gtgagcaagg caccctggt gcagaccaag     300
ggcactggtg cttctggctc ctttaaactc aacaagaagg cggcctccgg ggaagccaag     360
cccaaagcca agaaggcagg cgccgctaaa gctaagaagc ccgcggggc cacgcctaag     420
aaggccaaga aggctgcagg ggcgaaaaag gcagtgaaga agactccgaa gaaggcgaag     480
aagcccgcgg cggctggcgt caaaaaggtg gcgaagagcc ctaagaaggc caaggccgct     540
gccaaaccga aaaaggcaac caagagtcct gccaagccca aggcagttaa gccgaaggcg     600
gcaaagccca agccgctaa gcccaaagca gcaaaaccta agctgcaaa ggccaagaag     660
gcggctgcca aaagaagta g                                               681
```

<210> SEQ ID NO 13
<211> LENGTH: 219
<212> TYPE: PRT
<213> ORGANISM: Homo sapiens

<400> SEQUENCE: 13

```
Met Ser Glu Thr Ala Pro Ala Ala Pro Ala Ala Pro Ala Pro Ala Glu
1               5                   10                  15

Lys Thr Pro Val Lys Lys Lys Ala Arg Lys Ser Ala Gly Ala Ala Lys
            20                  25                  30

Arg Lys Ala Ser Gly Pro Pro Val Ser Glu Leu Ile Thr Lys Ala Val
        35                  40                  45

Ala Ala Ser Lys Glu Arg Ser Gly Val Ser Leu Ala Ala Leu Lys Lys
    50                  55                  60

Ala Leu Ala Ala Ala Gly Tyr Asp Val Glu Lys Asn Asn Ser Arg Ile
65                  70                  75                  80

Lys Leu Gly Leu Lys Ser Leu Val Ser Lys Gly Thr Leu Val Gln Thr
                85                  90                  95

Lys Gly Thr Gly Ala Ser Gly Ser Phe Lys Leu Asn Lys Lys Ala Ala
            100                 105                 110

Ser Gly Glu Ala Lys Pro Lys Ala Lys Lys Ala Gly Ala Ala Lys Ala
        115                 120                 125

Lys Lys Pro Ala Gly Ala Ala Lys Lys Pro Lys Lys Ala Thr Gly Ala
    130                 135                 140

Ala Thr Pro Lys Lys Ser Ala Lys Lys Thr Pro Lys Lys Ala Lys Lys
145                 150                 155                 160

Pro Ala Ala Ala Ala Gly Ala Lys Lys Ala Lys Ser Pro Lys Lys Ala
                165                 170                 175

Lys Ala Ala Lys Pro Lys Lys Ala Pro Lys Ser Pro Ala Ala Ala Lys
            180                 185                 190

Ala Val Lys Pro Lys Ala Ala Lys Pro Lys Thr Ala Lys Pro Lys Ala
        195                 200                 205

Ala Lys Pro Lys Lys Ala Ala Ala Lys Lys Lys
    210                 215
```

<210> SEQ ID NO 14
<211> LENGTH: 4

```
<212> TYPE: PRT
<213> ORGANISM: Artificial Sequence
<220> FEATURE:
<223> OTHER INFORMATION: Reducing active site of Thioredoxin-A

<400> SEQUENCE: 14

Cys Gly Pro Cys
 1
```